(12) United States Patent
Welsch et al.

(10) Patent No.: US 7,115,378 B2
(45) Date of Patent: Oct. 3, 2006

(54) PEPTIDE BIOMARKER AND METHOD OF IDENTIFICATION

(75) Inventors: Dean J. Welsch, St. Peters, MO (US); Kevin L. Duffin, Manchester, MO (US); Olga V. Nemirovskiy, Wildwood, MO (US); Dawn R. Dufield, O'Fallon, MO (US); Teresa Sunyer, Wildwood, MO (US); Carol Pearcy Howard, Fenton, MO (US)

(73) Assignee: Pharmacia Corporation, St. Louis, MO (US)

( * ) Notice: Subject to any disclaimer, the term of this patent is extended or adjusted under 35 U.S.C. 154(b) by 89 days.

(21) Appl. No.: 10/233,885

(22) Filed: Sep. 3, 2002

(65) Prior Publication Data

US 2003/0049715 A1 Mar. 13, 2003

Related U.S. Application Data

(60) Provisional application No. 60/316,554, filed on Aug. 31, 2001.

(51) Int. Cl.
*G01N 33/53* (2006.01)
(52) U.S. Cl. ............. 435/7.1; 435/7.2; 435/7.9; 435/7.92; 435/7.93; 436/578; 436/538; 436/15; 436/86
(58) Field of Classification Search ............. 435/7.1, 435/7.2, 7.9, 7.92, 7.93; 436/518, 538, 15, 436/86
See application file for complete search history.

(56) References Cited

U.S. PATENT DOCUMENTS

| | | | |
|---|---|---|---|
| 5,140,103 A | 8/1992 | Eyre | |
| 5,532,169 A | 7/1996 | Eyre | |
| 5,641,837 A | 6/1997 | Eyre | |
| 5,702,909 A | 12/1997 | Eyre | |
| 6,027,903 A | 2/2000 | Eyre | |
| 6,030,792 A | 2/2000 | Otterness et al. | |
| 6,107,047 A | 8/2000 | Fledelius et al. | |
| 6,110,689 A | 8/2000 | Qvist et al. | |
| 6,132,976 A | 10/2000 | Poole et al. | |
| 6,322,970 B1 | 11/2001 | Little et al. | |
| 6,642,007 B1 | 11/2003 | Saltarelli et al. | |

FOREIGN PATENT DOCUMENTS

GB WO 94/14070 * 6/1994

OTHER PUBLICATIONS

R.C. Billinghurst, et al., *J. Clin. Invest.* 99: 1534-1545 (1997).
I.G. Otterness, et al., *Matrix Biology* 18: 331-341 (1999).
D. Knapp, *Handbook of Analytical Derivation Reactions*, John Wiley and Sons, Inc. (1979).
B. Keil, *Specificity of proteolysis*, Springer-Verlag Berlin-Heidelberg, New York, 335 (1992).
J. Birktoft and K. Breddan, Glutamyl endopeptidases, *Methods of Enzymology*, 244: 114-126 (1994).
J. Houmard and G. Drapeau, Stapylococcal protease: a proteolytic enzyme specific for glutamoyl bonds, *Proceedings for the National Academy of Science in the United States of America*, 69: 3506-3509 (1972).
Li, A. et al., Chemical cleavage at aspartyl residues for protein identification, *Anal. Chem* 73: 5395-5402 (2001).
M. Diamant, et al., Elevated matrix metalloproteinase-2 and -9 in urine, but not in serum, are markers of Type 1 diabetic nephropathy, *Diabetic Medicine* 18: 423-426 (2001).
J.T. Downs, et al. Analysis of collagenase-cleavage of type II collagen using a neoepitope ELISA, *Journal of Immunological Methods* 247, 25-34 http://www.elsevier.nl/locate/jim.
D. Tabb, Scaling Performance for Scientific Computing: A Beowulf Cluster for Signal Processing 2 pages, (May 20, 2000).
"An Introduction to Mass Spectrometry" http://depts.washington.edu/~yeastrc/ms_home.htm 2 pages.
"An Introduction to Mass Spectrometry (cont.); IV. Determining the Amino Acid Sequence of a Polypeptide (cont.)" http://depts.washington.edu/~yeastrc/ms_lesson6.html.
"An Introduction to Mass Spectrometry (cont.); IV. Determining the Amino Acid Sequence of a Polypeptide (cont.)" http://depts.washington.edu/~yeastrc/ms_lesson7.html.
"An Introduction to Mass Spectrometry (cont.); III. Tandem Mass Spectrometers" http://depts.washington.edu/~yeastrc/ms_lesson4.html.
"An Introduction to Mass Spectrometry (cont.); IV. Determining the Amino Acid Sequence of a Polypeptide" http://depts.washington.edu/~yeastrc/ms_lesson5.html.
"An Introduction to Mass Spectrometry (cont.); IV. Determining the Amino Acid Sequence of a Polypeptide (cont.)" http://depts.washington.edu/~yeastrc/ms_lesson8.html.
"An Introduction to Mass Spectrometry (cont.); IV. Determining the Amino Acid Sequence of a Polypeptide (cont.)" http://depts.washington.edu/~yeastrc/ms_lesson9.html.
An Introduction to Mass Spectrometry (cont.); V. Conclusion http://depts.washington.edu/~yeastrc/ms_lesson10.html.

(Continued)

*Primary Examiner*—Long V. Le
*Assistant Examiner*—Jacob Cheu
(74) *Attorney, Agent, or Firm*—Pharmacia Corporation

(57) ABSTRACT

A method for identifying and quantifying peptides resulting from enzyme cleavage of collagen type II by mass spectrometric analysis to detect characteristic peptide fragments of a carboxy-terminus having known mass to charge ratios to identify the peptide having that carboxy-terminus. Identification and quantification of the peptides in a biological sample is used to assess activity of proteolytic enzymes in diseases or physiological conditions such as osteoarthritis and rheumatoid arthritis and to assess the efficacy of enzyme blocking agents.

17 Claims, 12 Drawing Sheets

OTHER PUBLICATIONS

"Peptides and Proteins Analysis by MS" http://www.micromass.co.uk/basics/pepbtb.2.html (15pgs).

"An Introduction to Biotechnology" http://www.micromass.co.uk/basics/biotech.2.html (15pgs).

"Mass Spectrometry—A Basic Overview" http://www.duke.edu/~mdfeezeor/NSHome/inform/basicms.html (3 pgs).

"Peptides and Proteins Analysis by MS" http://www.micromass.co.uk/basics/pepbtb.1.html (2pgs).

"Tandem Mass Spectrometry" http://www.duke.edu/~mdfeexor/NSHome/inform/smsl.html (15pgs).

"Protein Primary Structure" http://www-isu.indstate.edu/thcme/mwking/protein-structure.html (16 pgs).

* cited by examiner

MS/MS Spectrum of Collagen Type II Peptide in Human OA Urine

LQGPAGPPGEKGEHyPGDDGPSGAEGPHyPGPQG

*Precursor Ion: m/z 914.4 for 3+*

SEQUENCE LISTING

<160> NUMBER OF SEQ ID NOS: 44

<210> SEQ ID NO 1
<211> LENGTH: 7
<212> TYPE: PRT

```
<213> ORGANISM: homo sapiens
<220> FEATURE:
<221> NAME/KEY: MOD_RES
<222> LOCATION: (3)..(3)
<223> OTHER INFORMATION: Pro or 4Hyp

<400> SEQUENCE: 1

Gly Pro Pro Gly Pro Gln Gly
1               5

<210> SEQ ID NO 2
<211> LENGTH: 30
<212> TYPE: PRT
<213> ORGANISM: homo sapiens
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 2

Leu Gln Gly Pro Ala Gly Pro Pro Gly Glu Lys Gly Glu Pro Gly Asp
1               5                   10                  15

Asp Gly Pro Ser Gly Ala Glu Gly Pro Pro Gly Pro Gln Gly
            20                  25                  30

<210> SEQ ID NO 3
<211> LENGTH: 30
<212> TYPE: PRT
<213> ORGANISM: bos taurus
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 3

Leu Gln Gly Pro Ala Gly Pro Pro Gly Glu Lys Gly Glu Pro Gly Asp
1               5                   10                  15

Asp Gly Pro Ser Gly Pro Asp Gly Pro Pro Gly Pro Gln Gly
            20                  25                  30

<210> SEQ ID NO 4
<211> LENGTH: 30
<212> TYPE: PRT
<213> ORGANISM: canis familiaris
<220> FEATURE:
<221> NAME/KEY: MOD_RES
<222> LOCATION: (8)..(8)
```

```
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 4

Leu Gln Gly Pro Ala Gly Pro Pro Gly Glu Lys Gly Glu Pro Gly Asp
1               5                   10                  15

Asp Gly Pro Ser Gly Pro Asp Gly Pro Pro Gly Pro Gln Gly
            20                  25                  30

<210> SEQ ID NO 5
<211> LENGTH: 3
<212> TYPE: PRT
<213> ORGANISM: homo sapiens

<400> SEQUENCE: 5

Pro Gln Gly
1

<210> SEQ ID NO 6
<211> LENGTH: 5
<212> TYPE: PRT
<213> ORGANISM: homo sapiens

<400> SEQUENCE: 6

Pro Gly Pro Gln Gly
1               5

<210> SEQ ID NO 7
<211> LENGTH: 6
<212> TYPE: PRT
<213> ORGANISM: homo sapiens
<220> FEATURE:
<221> NAME/KEY: MOD_RES
<222> LOCATION: (1)..(1)
<223> OTHER INFORMATION: Pro or 4Hyp

<400> SEQUENCE: 7

Pro Pro Gly Pro Gln Gly
1               5

<210> SEQ ID NO 8
<211> LENGTH: 30
<212> TYPE: PRT
<213> ORGANISM: rattus sp.
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
```

```
<223> OTHER INFORMATION: Pro or 4Hyp

<400> SEQUENCE: 8

Leu Gln Gly Pro Ala Gly Ala Pro Gly Glu Lys Gly Glu Pro Gly Asp
1               5                   10                  15

Asp Gly Pro Ser Gly Ser Asp Gly Pro Pro Gly Pro Gln Gly
            20                  25                  30

<210> SEQ ID NO 9
<211> LENGTH: 30
<212> TYPE: PRT
<213> ORGANISM: Oryctolagus cuniculus
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 9

Leu Gln Gly Pro Ala Gly Pro Pro Gly Leu Lys Gly Glu Pro Gly Asp
1               5                   10                  15

Ser Gly Pro Ser Gly Ala Asp Gly Pro Pro Gly Pro Gln Gly
            20                  25                  30

<210> SEQ ID NO 10
<211> LENGTH: 30
<212> TYPE: PRT
<213> ORGANISM: mus sp.
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 10

Leu Glu Gly Pro Ala Gly Ala Pro Gly Glu Lys Gly Glu Pro Gly Asp
1               5                   10                  15

Asp Gly Pro Ser Gly Leu Asp Gly Pro Pro Gly Pro Gln Gly
            20                  25                  30

<210> SEQ ID NO 11
<211> LENGTH: 30
<212> TYPE: PRT
<213> ORGANISM: equus sp.
<220> FEATURE:
<221> NAME/KEY: MOD_RES
<222> LOCATION: (8)..(8)
<223> OTHER INFORMATION: Pro or 4Hyp
```

```
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 11

Leu Gln Gly Pro Ala Gly Pro Pro Gly Glu Lys Gly Glu Pro Gly Asp
1               5                  10                  15

Asp Gly Pro Ser Gly Pro Asp Gly Pro Pro Gly Pro Gln Gly
            20                  25                  30

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide collagent type I fragment
<220> FEATURE:
<221> NAME/KEY: MOD_RES
<222> LOCATION: (3)..(3)
<223> OTHER INFORMATION: Pro or 4Hyp

<400> SEQUENCE: 12

Gly Thr Pro Gly Pro Gln Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide collagen type III fragment
<220> FEATURE:
<221> NAME/KEY: MOD_RES
<222> LOCATION: (3)..(3)
<223> OTHER INFORMATION: Pro or 4Hyp

<400> SEQUENCE: 13

Gly Ala Pro Gly Pro Leu Gly
1               5

<210> SEQ ID NO 14
<211> LENGTH: 31
<212> TYPE: PRT
<213> ORGANISM: Artificial Sequence
<220> FEATURE:
<223> OTHER INFORMATION: Synthetic peptide collagen type II fragment
<220> FEATURE:
<221> NAME/KEY: MOD_RES
<222> LOCATION: (9)..(9)
<223> OTHER INFORMATION: Pro or 4Hyp
<220> FEATURE:
<221> NAME/KEY: MOD_RES
<222> LOCATION: (12)..(12)
<223> OTHER INFORMATION: Lys or Hyl
<220> FEATURE:
<221> NAME/KEY: MOD_RES
<222> LOCATION: (15)..(15)
<223> OTHER INFORMATION: Pro or 4Hyp
<220> FEATURE:
<221> NAME/KEY: MOD_RES
<222> LOCATION: (27)..(27)
<223> OTHER INFORMATION: Pro or 4Hyp
```

-continued

```
<400> SEQUENCE: 14

Val Leu Gln Gly Pro Ala Gly Pro Pro Gly Glu Lys Gly Glu Pro Gly
1               5                   10                  15

Asp Asp Gly Pro Ser Gly Ala Glu Gly Pro Pro Gly Pro Gln Gly
            20                  25                  30

<210> SEQ ID NO 15
<211> LENGTH: 47
<212> TYPE: PRT
<213> ORGANISM: homo sapiens
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (16)..(16)
<223> OTHER INFORMATION: Pro or 4Hyp
<220> FEATURE:
<221> NAME/KEY: MOD_RES
<222> LOCATION: (25)..(25)
<223> OTHER INFORMATION: Pro or 4Hyp
<220> FEATURE:
<221> NAME/KEY: MOD_RES
<222> LOCATION: (31)..(31)
<223> OTHER INFORMATION: Pro or 4Hyp
<220> FEATURE:
<221> NAME/KEY: MOD_RES
<222> LOCATION: (43)..(43)
<223> OTHER INFORMATION: Pro or 4Hyp

<400> SEQUENCE: 15

Lys Gly Ala Arg Gly Asp Ser Gly Pro Pro Gly Arg Ala Gly Glu Pro
1               5                   10                  15

Gly Leu Gln Gly Pro Ala Gly Pro Pro Gly Glu Lys Gly Glu Pro Gly
            20                  25                  30

Asp Asp Gly Pro Ser Gly Ala Glu Gly Pro Pro Gly Pro Gln Gly
        35                  40                  45

<210> SEQ ID NO 16
<211> LENGTH: 45
<212> TYPE: PRT
<213> ORGANISM: homo sapiens
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (23)..(23)
<223> OTHER INFORMATION: Pro or 4Hyp
<220> FEATURE:
<221> NAME/KEY: MOD_RES
<222> LOCATION: (26)..(26)
<223> OTHER INFORMATION: Lys or Hyl
<220> FEATURE:
<221> NAME/KEY: MOD_RES
<222> LOCATION: (29)..(29)
<223> OTHER INFORMATION: Pro or 4Hyp
<220> FEATURE:
<221> NAME/KEY: MOD_RES
<222> LOCATION: (41)..(41)
<223> OTHER INFORMATION: Pro or 4Hyp

<400> SEQUENCE: 16

Ala Arg Gly Asp Ser Gly Pro Pro Gly Arg Ala Gly Glu Pro Gly Leu
1               5                   10                  15
```

-continued

```
Gln Gly Pro Ala Gly Pro Pro Gly Glu Lys Gly Glu Pro Gly Asp Asp
            20                  25                  30
Gly Pro Ser Gly Ala Glu Gly Pro Pro Gly Pro Gln Gly
        35                  40                  45

<210> SEQ ID NO 17
<211> LENGTH: 28
<212> TYPE: PRT
<213> ORGANISM: homo sapiens
<220> FEATURE:
<221> NAME/KEY: MOD_RES
<222> LOCATION: (12)..(12)
<223> OTHER INFORMATION: Pro or 4Hyp
<220> FEATURE:
<221> NAME/KEY: MOD_RES
<222> LOCATION: (24)..(24)
<223> OTHER INFORMATION: Pro or 4Hyp

<400> SEQUENCE: 17

Gly Pro Ala Gly Pro Pro Gly Glu Lys Gly Glu Pro Gly Asp Asp Gly
1               5                   10                  15
Pro Ser Gly Ala Glu Gly Pro Pro Gly Pro Gln Gly
            20                  25

<210> SEQ ID NO 18
<211> LENGTH: 47
<212> TYPE: PRT
<213> ORGANISM: canis familiaris
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (16)..(16)
<223> OTHER INFORMATION: Pro or 4Hyp
<220> FEATURE:
<221> NAME/KEY: MOD_RES
<222> LOCATION: (25)..(25)
<223> OTHER INFORMATION: Pro or 4Hyp
<220> FEATURE:
<221> NAME/KEY: MOD_RES
<222> LOCATION: (28)..(28)
<223> OTHER INFORMATION: Lys or Hyl
<220> FEATURE:
<221> NAME/KEY: MOD_RES
<222> LOCATION: (31)..(31)
<223> OTHER INFORMATION: Pro or 4Hyp
<220> FEATURE:
<221> NAME/KEY: MOD_RES
<222> LOCATION: (43)..(43)
<223> OTHER INFORMATION: Pro or 4Hyp

<400> SEQUENCE: 18

Lys Gly Ala Arg Gly Asp Ser Gly Pro Pro Gly Arg Ala Gly Asp Pro
1               5                   10                  15
Gly Leu Gln Gly Pro Ala Gly Pro Pro Gly Glu Lys Gly Glu Pro Gly
            20                  25                  30
Asp Asp Gly Pro Ser Gly Pro Asp Gly Pro Pro Gly Pro Gln Gly
        35                  40                  45

<210> SEQ ID NO 19
<211> LENGTH: 45
<212> TYPE: PRT
<213> ORGANISM: canis familiaris
<220> FEATURE:
<221> NAME/KEY: MOD_RES
<222> LOCATION: (8)..(8)
<223> OTHER INFORMATION: Pro or 4Hyp
```

```
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (23)..(23)
<223> OTHER INFORMATION: Pro or 4Hyp
<220> FEATURE:
<221> NAME/KEY: MOD_RES
<222> LOCATION: (26)..(26)
<223> OTHER INFORMATION: Lys or Hyl
<220> FEATURE:
<221> NAME/KEY: MOD_RES
<222> LOCATION: (29)..(29)
<223> OTHER INFORMATION: Pro or 4Hyp
<220> FEATURE:
<221> NAME/KEY: MOD_RES
<222> LOCATION: (41)..(41)
<223> OTHER INFORMATION: Pro or 4Hyp

<400> SEQUENCE: 19

Ala Arg Gly Asp Ser Gly Pro Pro Gly Arg Ala Gly Asp Pro Gly Leu
1               5                   10                  15

Gln Gly Pro Ala Gly Pro Pro Gly Glu Lys Gly Glu Pro Gly Asp Asp
            20                  25                  30

Gly Pro Ser Gly Pro Asp Gly Pro Pro Gly Pro Gln Gly
        35                  40                  45

<210> SEQ ID NO 20
<211> LENGTH: 26
<212> TYPE: PRT
<213> ORGANISM: canis familiaris
<220> FEATURE:
<221> NAME/KEY: MOD_RES
<222> LOCATION: (4)..(4)
<223> OTHER INFORMATION: Pro or 4Hyp
<220> FEATURE:
<221> NAME/KEY: MOD_RES
<222> LOCATION: (7)..(7)
<223> OTHER INFORMATION: Lys or Hyl
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (22)..(22)
<223> OTHER INFORMATION: Pro or 4Hyp

<400> SEQUENCE: 20

Ala Gly Pro Pro Gly Glu Lys Gly Glu Pro Gly Asp Asp Gly Pro Ser
1               5                   10                  15

Gly Pro Asp Gly Pro Pro Gly Pro Gln Gly
            20                  25

<210> SEQ ID NO 21
<211> LENGTH: 24
<212> TYPE: PRT
<213> ORGANISM: canis familiaris
<220> FEATURE:
<221> NAME/KEY: MOD_RES
<222> LOCATION: (2)..(2)
<223> OTHER INFORMATION: Pro or 4Hyp
<220> FEATURE:
<221> NAME/KEY: MOD_RES
<222> LOCATION: (5)..(5)
<223> OTHER INFORMATION: Lys or Hyl
<220> FEATURE:
<221> NAME/KEY: MOD_RES
<222> LOCATION: (8)..(8)
<223> OTHER INFORMATION: Pro or 4Hyp
```

-continued

```
<220> FEATURE:
<221> NAME/KEY: MOD_RES
<222> LOCATION: (20)..(20)
<223> OTHER INFORMATION: Pro or 4Hyp

<400> SEQUENCE: 21

Pro Pro Gly Glu Lys Gly Glu Pro Gly Asp Asp Gly Pro Ser Gly Pro
1               5                   10                  15
Asp Gly Pro Pro Gly Pro Gln Gly
            20

<210> SEQ ID NO 22
<211> LENGTH: 21
<212> TYPE: PRT
<213> ORGANISM: canis familiaris
<220> FEATURE:
<221> NAME/KEY: MOD_RES
<222> LOCATION: (2)..(2)
<223> OTHER INFORMATION: Lys or Hyl
<220> FEATURE:
<221> NAME/KEY: MOD_RES
<222> LOCATION: (5)..(5)
<223> OTHER INFORMATION: Pro or 4Hyp
<220> FEATURE:
<221> NAME/KEY: MOD_RES
<222> LOCATION: (17)..(17)
<223> OTHER INFORMATION: Pro or 4Hyp

<400> SEQUENCE: 22

Glu Lys Gly Glu Pro Gly Asp Asp Gly Pro Ser Gly Pro Asp Gly Pro
1               5                   10                  15
Pro Gly Pro Gln Gly
            20

<210> SEQ ID NO 23
<211> LENGTH: 47
<212> TYPE: PRT
<213> ORGANISM: felis catus
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (16)..(16)
<223> OTHER INFORMATION: Pro or 4Hyp
<220> FEATURE:
<221> NAME/KEY: MOD_RES
<222> LOCATION: (25)..(25)
<223> OTHER INFORMATION: Pro or 4Hyp
<220> FEATURE:
<221> NAME/KEY: MOD_RES
<222> LOCATION: (28)..(28)
<223> OTHER INFORMATION: Lys or Hyl
<220> FEATURE:
<221> NAME/KEY: MOD_RES
<222> LOCATION: (31)..(31)
<223> OTHER INFORMATION: Pro or 4Hyp
<220> FEATURE:
<221> NAME/KEY: MOD_RES
<222> LOCATION: (43)..(43)
<223> OTHER INFORMATION: Pro or 4Hyp

<400> SEQUENCE: 23

Lys Gly Ala Arg Gly Asp Ser Gly Pro Pro Gly Arg Ala Gly Asp Pro
1               5                   10                  15
Gly Leu Gln Gly Pro Ala Gly Pro Pro Gly Glu Lys Gly Glu Pro Gly
            20                  25                  30
Asp Asp Gly Pro Ser Gly Pro Asp Gly Pro Pro Gly Pro Gln Gly
        35                  40                  45
```

```
<210> SEQ ID NO 24
<211> LENGTH: 45
<212> TYPE: PRT
<213> ORGANISM: felis catus
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (23)..(23)
<223> OTHER INFORMATION: Pro or 4Hyp
<220> FEATURE:
<221> NAME/KEY: MOD_RES
<222> LOCATION: (26)..(26)
<223> OTHER INFORMATION: Lys or Hyl
<220> FEATURE:
<221> NAME/KEY: MOD_RES
<222> LOCATION: (29)..(29)
<223> OTHER INFORMATION: Pro or 4Hyp
<220> FEATURE:
<221> NAME/KEY: MOD_RES
<222> LOCATION: (41)..(41)
<223> OTHER INFORMATION: Pro or 4Hyp

<400> SEQUENCE: 24

Ala Arg Gly Asp Ser Gly Pro Pro Gly Arg Ala Gly Asp Pro Gly Leu
1               5                   10                  15

Gln Gly Pro Ala Gly Pro Pro Gly Glu Lys Gly Glu Pro Gly Asp Asp
            20                  25                  30

Gly Pro Ser Gly Pro Asp Gly Pro Gly Pro Gln Gly
        35                  40                  45

<210> SEQ ID NO 25
<211> LENGTH: 30
<212> TYPE: PRT
<213> ORGANISM: felis catus
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (11)..(11)
<223> OTHER INFORMATION: Lys or Hyl
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (26)..(26)
<223> OTHER INFORMATION: Pro or 4Hyp

<400> SEQUENCE: 25

Leu Gln Gly Pro Ala Gly Pro Pro Gly Glu Lys Gly Glu Pro Gly Asp
1               5                   10                  15

Asp Gly Pro Ser Gly Pro Asp Gly Pro Pro Gly Pro Gln Gly
            20                  25                  30

<210> SEQ ID NO 26
<211> LENGTH: 26
<212> TYPE: PRT
<213> ORGANISM: felis catus
<220> FEATURE:
<221> NAME/KEY: MOD_RES
```

```
<222> LOCATION: (4)..(4)
<223> OTHER INFORMATION: Pro or 4Hyp
<220> FEATURE:
<221> NAME/KEY: MOD_RES
<222> LOCATION: (7)..(7)
<223> OTHER INFORMATION: Lys or Hyl
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (22)..(22)
<223> OTHER INFORMATION: Pro or 4Hyp

<400> SEQUENCE: 26

Ala Gly Pro Pro Gly Glu Lys Gly Glu Pro Gly Asp Asp Gly Pro Ser
1               5                   10                  15

Gly Pro Asp Gly Pro Pro Gly Pro Gln Gly
            20                  25

<210> SEQ ID NO 27
<211> LENGTH: 24
<212> TYPE: PRT
<213> ORGANISM: felis catus
<220> FEATURE:
<221> NAME/KEY: MOD_RES
<222> LOCATION: (2)..(2)
<223> OTHER INFORMATION: Pro or 4Hyp
<220> FEATURE:
<221> NAME/KEY: MOD_RES
<222> LOCATION: (5)..(5)
<223> OTHER INFORMATION: Lys or Hyl
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (20)..(20)
<223> OTHER INFORMATION: Pro or 4Hyp

<400> SEQUENCE: 27

Pro Pro Gly Glu Lys Gly Glu Pro Gly Asp Asp Gly Pro Ser Gly Pro
1               5                   10                  15

Asp Gly Pro Pro Gly Pro Gln Gly
            20

<210> SEQ ID NO 28
<211> LENGTH: 21
<212> TYPE: PRT
<213> ORGANISM: felis catus
<220> FEATURE:
<221> NAME/KEY: MOD_RES
<222> LOCATION: (2)..(2)
<223> OTHER INFORMATION: Lys or Hyl
<220> FEATURE:
<221> NAME/KEY: MOD_RES
<222> LOCATION: (5)..(5)
<223> OTHER INFORMATION: Pro or 4Hyp
<220> FEATURE:
<221> NAME/KEY: MOD_RES
<222> LOCATION: (17)..(17)
<223> OTHER INFORMATION: Pro or 4Hyp

<400> SEQUENCE: 28

Glu Lys Gly Glu Pro Gly Asp Asp Gly Pro Ser Gly Pro Asp Gly Pro
1               5                   10                  15

Pro Gly Pro Gln Gly
            20
```

<210> SEQ ID NO 29
<211> LENGTH: 47
<212> TYPE: PRT
<213> ORGANISM: equus sp.
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (16)..(16)
<223> OTHER INFORMATION: Pro or 4Hyp
<220> FEATURE:
<221> NAME/KEY: MOD_RES
<222> LOCATION: (25)..(25)
<223> OTHER INFORMATION: Pro or 4Hyp
<220> FEATURE:
<221> NAME/KEY: MOD_RES
<222> LOCATION: (28)..(28)
<223> OTHER INFORMATION: Lys or Hyl
<220> FEATURE:
<221> NAME/KEY: MOD_RES
<222> LOCATION: (31)..(31)
<223> OTHER INFORMATION: Pro or 4Hyp
<220> FEATURE:
<221> NAME/KEY: MOD_RES
<222> LOCATION: (43)..(43)
<223> OTHER INFORMATION: Pro or 4Hyp

<400> SEQUENCE: 29

Lys Gly Ala Arg Gly Asp Ser Gly Pro Pro Gly Arg Ala Gly Asp Pro
1               5                   10                  15
Gly Leu Gln Gly Pro Ala Gly Pro Pro Gly Glu Lys Gly Glu Pro Gly
            20                  25                  30
Asp Asp Gly Pro Ser Gly Pro Asp Gly Pro Pro Gly Pro Gln Gly
        35                  40                  45

<210> SEQ ID NO 30
<211> LENGTH: 45
<212> TYPE: PRT
<213> ORGANISM: equus sp.
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (23)..(23)
<223> OTHER INFORMATION: Pro or 4Hyp
<220> FEATURE:
<221> NAME/KEY: MOD_RES
<222> LOCATION: (26)..(26)
<223> OTHER INFORMATION: Lys or Hyl
<220> FEATURE:
<221> NAME/KEY: MOD_RES
<222> LOCATION: (29)..(29)
<223> OTHER INFORMATION: Pro or 4Hyp
<220> FEATURE:
<221> NAME/KEY: MOD_RES
<222> LOCATION: (41)..(41)
<223> OTHER INFORMATION: Pro or 4Hyp

<400> SEQUENCE: 30

Ala Arg Gly Asp Ser Gly Pro Pro Gly Arg Ala Gly Asp Pro Gly Leu
1               5                   10                  15
Gln Gly Pro Ala Gly Pro Pro Gly Glu Lys Gly Glu Pro Gly Asp Asp
            20                  25                  30

Gly Pro Ser Gly Pro Asp Gly Pro Pro Gly Pro Gln Gly
        35              40              45

<210> SEQ ID NO 31
<211> LENGTH: 26
<212> TYPE: PRT
<213> ORGANISM: equus sp.
<220> FEATURE:
<221> NAME/KEY: MOD_RES
<222> LOCATION: (4)..(4)
<223> OTHER INFORMATION: Pro or 4Hyp
<220> FEATURE:
<221> NAME/KEY: MOD_RES
<222> LOCATION: (7)..(7)
<223> OTHER INFORMATION: Lys or Hyl
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (22)..(22)
<223> OTHER INFORMATION: Pro or 4Hyp

<400> SEQUENCE: 31

Ala Gly Pro Pro Gly Glu Lys Gly Glu Pro Gly Asp Asp Gly Pro Ser
1               5                   10                  15

Gly Pro Asp Gly Pro Pro Gly Pro Gln Gly
            20                  25

<210> SEQ ID NO 32
<211> LENGTH: 24
<212> TYPE: PRT
<213> ORGANISM: equus sp.
<220> FEATURE:
<221> NAME/KEY: MOD_RES
<222> LOCATION: (2)..(2)
<223> OTHER INFORMATION: Pro or 4Hyp
<220> FEATURE:
<221> NAME/KEY: MOD_RES
<222> LOCATION: (5)..(5)
<223> OTHER INFORMATION: Lys or Hyl
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (20)..(20)
<223> OTHER INFORMATION: Pro or 4Hyp

<400> SEQUENCE: 32

Pro Pro Gly Glu Lys Gly Glu Pro Gly Asp Asp Gly Pro Ser Gly Pro
1               5                   10                  15

Asp Gly Pro Pro Gly Pro Gln Gly
            20

<210> SEQ ID NO 33
<211> LENGTH: 21
<212> TYPE: PRT
<213> ORGANISM: equus sp.
<220> FEATURE:
<221> NAME/KEY: MOD_RES
<222> LOCATION: (2)..(2)
<223> OTHER INFORMATION: Lys or Hyl
<220> FEATURE:
<221> NAME/KEY: MOD_RES
<222> LOCATION: (5)..(5)
<223> OTHER INFORMATION: Pro or 4Hyp
<220> FEATURE:
<221> NAME/KEY: MOD_RES
<222> LOCATION: (17)..(17)

-continued

```
<223> OTHER INFORMATION: Pro or 4Hyp

<400> SEQUENCE: 33

Glu Lys Gly Glu Pro Gly Asp Asp Gly Pro Ser Gly Pro Asp Gly Pro
1               5                   10                  15

Pro Gly Pro Gln Gly
            20

<210> SEQ ID NO 34
<211> LENGTH: 47
<212> TYPE: PRT
<213> ORGANISM: bos taurus
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (16)..(16)
<223> OTHER INFORMATION: Pro or 4Hyp
<220> FEATURE:
<221> NAME/KEY: MOD_RES
<222> LOCATION: (25)..(25)
<223> OTHER INFORMATION: Pro or 4Hyp
<220> FEATURE:
<221> NAME/KEY: MOD_RES
<222> LOCATION: (28)..(28)
<223> OTHER INFORMATION: Lys or Hyl
<220> FEATURE:
<221> NAME/KEY: MOD_RES
<222> LOCATION: (31)..(31)
<223> OTHER INFORMATION: Pro or 4Hyp
<220> FEATURE:
<221> NAME/KEY: MOD_RES
<222> LOCATION: (43)..(43)
<223> OTHER INFORMATION: Pro or 4Hyp

<400> SEQUENCE: 34

Lys Gly Ala Arg Gly Asp Ser Gly Pro Pro Gly Arg Ala Gly Asp Pro
1               5                   10                  15

Gly Leu Gln Gly Pro Ala Gly Pro Pro Gly Glu Lys Gly Glu Pro Gly
            20                  25                  30

Asp Asp Gly Pro Ser Gly Pro Asp Gly Pro Pro Gly Pro Gln Gly
        35                  40                  45

<210> SEQ ID NO 35
<211> LENGTH: 45
<212> TYPE: PRT
<213> ORGANISM: bos taurus
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (23)..(23)
<223> OTHER INFORMATION: Pro or 4Hyp
<220> FEATURE:
<221> NAME/KEY: MOD_RES
<222> LOCATION: (26)..(26)
<223> OTHER INFORMATION: Lys or Hyl
<220> FEATURE:
<221> NAME/KEY: MOD_RES
<222> LOCATION: (29)..(29)
<223> OTHER INFORMATION: Pro or 4Hyp
<220> FEATURE:
<221> NAME/KEY: MOD_RES
<222> LOCATION: (41)..(41)
```

-continued

```
<223> OTHER INFORMATION: Pro or 4Hyp

<400> SEQUENCE: 35

Ala Arg Gly Asp Ser Gly Pro Pro Gly Arg Ala Gly Asp Pro Gly Leu
1               5                   10                  15

Gln Gly Pro Ala Gly Pro Pro Gly Glu Lys Gly Glu Pro Gly Asp Asp
            20                  25                  30

Gly Pro Ser Gly Pro Asp Gly Pro Gly Pro Gln Gly
        35                  40                  45

<210> SEQ ID NO 36
<211> LENGTH: 26
<212> TYPE: PRT
<213> ORGANISM: bos taurus
<220> FEATURE:
<221> NAME/KEY: MOD_RES
<222> LOCATION: (4)..(4)
<223> OTHER INFORMATION: Pro or 4Hyp
<220> FEATURE:
<221> NAME/KEY: MOD_RES
<222> LOCATION: (7)..(7)
<223> OTHER INFORMATION: Lys or Hyl
<220> FEATURE:
<221> NAME/KEY: MOD_RES
<222> LOCATION: (10)..(10)
<223> OTHER INFORMATION: Pro or 4Hyp
<220> FEATURE:
<221> NAME/KEY: MOD_RES
<222> LOCATION: (22)..(22)
<223> OTHER INFORMATION: Pro or 4Hyp

<400> SEQUENCE: 36

Ala Gly Pro Pro Gly Glu Lys Gly Glu Pro Gly Asp Asp Gly Pro Ser
1               5                   10                  15

Gly Pro Asp Gly Pro Pro Gly Pro Gln Gly
            20                  25

<210> SEQ ID NO 37
<211> LENGTH: 24
<212> TYPE: PRT
<213> ORGANISM: bos taurus
<220> FEATURE:
<221> NAME/KEY: MOD_RES
<222> LOCATION: (2)..(2)
<223> OTHER INFORMATION: Pro or 4Hyp
<220> FEATURE:
<221> NAME/KEY: MOD_RES
<222> LOCATION: (5)..(5)
<223> OTHER INFORMATION: Lys or Hyl
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (20)..(20)
<223> OTHER INFORMATION: Pro or 4Hyp

<400> SEQUENCE: 37

Pro Pro Gly Glu Lys Gly Glu Pro Gly Asp Asp Gly Pro Ser Gly Pro
1               5                   10                  15

Asp Gly Pro Pro Gly Pro Gln Gly
            20

<210> SEQ ID NO 38
<211> LENGTH: 21
<212> TYPE: PRT
<213> ORGANISM: bos taurus
<220> FEATURE:
```

```
<221> NAME/KEY: MOD_RES
<222> LOCATION: (2)..(2)
<223> OTHER INFORMATION: Lys or Hyl
<220> FEATURE:
<221> NAME/KEY: MOD_RES
<222> LOCATION: (5)..(5)
<223> OTHER INFORMATION: Pro or 4Hyp
<220> FEATURE:
<221> NAME/KEY: MOD_RES
<222> LOCATION: (17)..(17)
<223> OTHER INFORMATION: Pro or 4Hyp

<400> SEQUENCE: 38

Glu Lys Gly Glu Pro Gly Asp Asp Gly Pro Ser Gly Pro Asp Gly Pro
1               5                   10                  15

Pro Gly Pro Gln Gly
            20

<210> SEQ ID NO 39
<211> LENGTH: 24
<212> TYPE: PRT
<213> ORGANISM: rattus sp.
<220> FEATURE:
<221> NAME/KEY: MOD_RES
<222> LOCATION: (2)..(2)
<223> OTHER INFORMATION: Pro or 4Hyp
<220> FEATURE:
<221> NAME/KEY: MOD_RES
<222> LOCATION: (5)..(5)
<223> OTHER INFORMATION: Lys or Hyl
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (20)..(20)
<223> OTHER INFORMATION: Pro or 4Hyp

<400> SEQUENCE: 39

Ala Pro Gly Glu Lys Gly Glu Pro Gly Asp Asp Gly Pro Ser Gly Ser
1               5                   10                  15

Asp Gly Pro Pro Gly Pro Gln Gly
            20

<210> SEQ ID NO 40
<211> LENGTH: 21
<212> TYPE: PRT
<213> ORGANISM: rattus sp.
<220> FEATURE:
<221> NAME/KEY: MOD_RES
<222> LOCATION: (2)..(2)
<223> OTHER INFORMATION: Lys or Hyl
<220> FEATURE:
<221> NAME/KEY: MOD_RES
<222> LOCATION: (5)..(5)
<223> OTHER INFORMATION: Pro or 4Hyp
<220> FEATURE:
<221> NAME/KEY: MOD_RES
<222> LOCATION: (17)..(17)
<223> OTHER INFORMATION: Pro or 4Hyp

<400> SEQUENCE: 40

Glu Lys Gly Glu Pro Gly Asp Asp Gly Pro Ser Gly Ser Asp Gly Pro
1               5                   10                  15

Pro Gly Pro Gln Gly
            20

<210> SEQ ID NO 41
<211> LENGTH: 19
```

```
<212> TYPE: PRT
<213> ORGANISM: rattus sp.
<220> FEATURE:
<221> NAME/KEY: MOD_RES
<222> LOCATION: (3)..(3)
<223> OTHER INFORMATION: Pro or 4Hyp
<220> FEATURE:
<221> NAME/KEY: MOD_RES
<222> LOCATION: (15)..(15)
<223> OTHER INFORMATION: Pro or 4Hyp

<400> SEQUENCE: 41

Gly Glu Pro Gly Asp Asp Gly Pro Ser Gly Ser Asp Gly Pro Pro Gly
1               5                   10                  15

Pro Gln Gly

<210> SEQ ID NO 42
<211> LENGTH: 14
<212> TYPE: PRT
<213> ORGANISM: rattus sp.
<220> FEATURE:
<221> NAME/KEY: MOD_RES
<222> LOCATION: (10)..(10)
<223> OTHER INFORMATION: Pro or 4Hyp

<400> SEQUENCE: 42

Asp Gly Pro Ser Gly Ser Asp Gly Pro Pro Gly Pro Gln Gly
1               5                   10

<210> SEQ ID NO 43
<211> LENGTH: 45
<212> TYPE: PRT
<213> ORGANISM: cavia porcellus
<220> FEATURE:
<221> NAME/KEY: MOD_RES
<222> LOCATION: (8)..(8)
<223> OTHER INFORMATION: Pro or 4Hyp
<220> FEATURE:
<221> NAME/KEY: MOD_RES
<222> LOCATION: (14)..(14)
<223> OTHER INFORMATION: Pro or 4Hyp
<220> FEATURE:
<221> NAME/KEY: MOD_RES
<222> LOCATION: (23)..(23)
<223> OTHER INFORMATION: Pro or 4Hyp
<220> FEATURE:
<221> NAME/KEY: MOD_RES
<222> LOCATION: (26)..(26)
<223> OTHER INFORMATION: Lys or Hyl
<220> FEATURE:
<221> NAME/KEY: MOD_RES
<222> LOCATION: (29)..(29)
<223> OTHER INFORMATION: Pro or 4Hyp
<220> FEATURE:
<221> NAME/KEY: MOD_RES
<222> LOCATION: (41)..(41)
<223> OTHER INFORMATION: Pro or 4Hyp

<400> SEQUENCE: 43

Val Arg Gly Asp Ser Gly Pro Pro Gly Arg Ala Gly Asp Pro Gly Leu
1               5                   10                  15

Gln Gly Pro Ala Gly Pro Pro Gly Glu Lys Gly Glu Pro Gly Asp Asp
                20                  25                  30

Gly Val Ser Gly Ala Asp Gly Pro Pro Gly Pro Gln Gly
            35                  40                  45

<210> SEQ ID NO 44
<211> LENGTH: 714
<212> TYPE: PRT
<213> ORGANISM: homo sapiens
```

-continued

<400> SEQUENCE: 44

```
Gly Pro Ile Gly Pro Gly Glu Arg Gly Ala Pro Gly Asn Arg Gly
  1               5                  10                  15

Phe Pro Gly Gln Asp Gly Leu Ala Gly Pro Lys Gly Ala Pro Gly Glu
                 20                  25                  30

Arg Gly Pro Ser Gly Leu Ala Gly Pro Lys Gly Ala Asn Gly Asp Pro
             35                  40                  45

Gly Arg Pro Gly Glu Pro Gly Leu Pro Gly Ala Arg Gly Leu Thr Gly
 50                  55                  60

Arg Pro Gly Asp Ala Gly Pro Gln Gly Lys Val Gly Pro Ser Gly Ala
 65                  70                  75                  80

Pro Gly Glu Asp Gly Arg Pro Gly Pro Gly Pro Gln Gly Ala Arg
                 85                  90                  95

Gly Gln Pro Gly Val Met Gly Phe Pro Gly Pro Lys Gly Ala Asn Gly
                100                 105                 110

Glu Pro Gly Lys Ala Gly Glu Lys Gly Leu Pro Gly Ala Pro Gly Leu
             115                 120                 125

Arg Gly Leu Pro Gly Lys Asp Gly Glu Thr Gly Ala Glu Gly Pro Pro
130                 135                 140

Gly Pro Ala Gly Pro Ala Gly Glu Arg Gly Glu Gln Gly Ala Pro Gly
145                 150                 155                 160

Pro Ser Gly Phe Gln Gly Leu Pro Gly Pro Pro Gly Pro Pro Gly Glu
                165                 170                 175

Ala Gly Lys Pro Gly Asp Gln Gly Val Pro Gly Glu Ala Gly Ala Pro
             180                 185                 190

Gly Leu Val Gly Pro Arg Gly Glu Arg Gly Phe Pro Gly Glu Arg Gly
         195                 200                 205

Ser Pro Gly Ala Gln Gly Leu Gln Gly Pro Arg Gly Leu Pro Gly Thr
210                 215                 220

Pro Gly Thr Asp Gly Pro Lys Gly Ala Ser Gly Pro Ala Gly Pro Pro
225                 230                 235                 240

Gly Ala Gln Gly Pro Pro Gly Leu Gln Gly Met Pro Gly Glu Arg Gly
                245                 250                 255

Ala Ala Gly Ile Ala Gly Pro Lys Gly Asp Arg Gly Asp Val Gly Glu
             260                 265                 270

Lys Gly Pro Glu Gly Ala Pro Gly Lys Asp Gly Ala Arg Gly Leu Thr
         275                 280                 285

Gly Pro Ile Gly Pro Pro Gly Pro Ala Gly Ala Asn Gly Glu Lys Gly
290                 295                 300

Glu Val Gly Pro Pro Gly Pro Ala Gly Ser Ala Gly Ala Arg Gly Ala
305                 310                 315                 320

Pro Gly Glu Arg Gly Glu Thr Gly Pro Pro Gly Pro Ala Gly Phe Ala
                325                 330                 335

Gly Pro Pro Gly Ala Asp Gly Gln Pro Gly Ala Lys Gly Glu Gln Gly
             340                 345                 350

Glu Ala Gly Gln Lys Gly Asp Ala Gly Ala Pro Gly Pro Gln Gly Pro
         355                 360                 365

Ser Gly Ala Pro Gly Pro Gln Gly Pro Thr Gly Val Thr Gly Pro Lys
370                 375                 380

Gly Ala Arg Gly Ala Gln Gly Pro Pro Gly Ala Thr Gly Phe Pro Gly
385                 390                 395                 400

Ala Ala Gly Arg Val Gly Pro Pro Gly Ser Asn Gly Asn Pro Gly Pro
```

-continued

```
            405                 410                 415
Pro Gly Pro Pro Gly Pro Ser Gly Lys Asp Gly Pro Lys Gly Ala Arg
            420                 425                 430
Gly Asp Ser Gly Pro Pro Gly Arg Ala Gly Glu Pro Gly Leu Gln Gly
            435                 440                 445
Pro Ala Gly Pro Pro Gly Glu Lys Gly Glu Pro Gly Asp Asp Gly Pro
            450                 455                 460
Ser Gly Ala Glu Gly Pro Pro Gly Pro Gln Gly Leu Ala Gly Gln Arg
465                 470                 475                 480
Gly Ile Val Gly Leu Pro Gly Gln Arg Gly Glu Arg Gly Phe Pro Gly
            485                 490                 495
Leu Pro Gly Pro Ser Gly Glu Pro Gly Gln Gln Gly Ala Pro Gly Ala
            500                 505                 510
Ser Gly Asp Arg Gly Pro Pro Gly Pro Val Gly Pro Pro Gly Leu Thr
            515                 520                 525
Gly Pro Ala Gly Glu Pro Gly Arg Glu Gly Ser Pro Gly Ala Asp Gly
            530                 535                 540
Pro Pro Gly Arg Asp Gly Ala Ala Gly Val Lys Gly Asp Arg Gly Glu
545                 550                 555                 560
Thr Gly Ala Val Gly Ala Pro Gly Ala Pro Gly Pro Pro Gly Ser Pro
            565                 570                 575
Gly Pro Ala Gly Pro Thr Gly Lys Gln Gly Asp Arg Gly Glu Ala Gly
            580                 585                 590
Ala Gln Gly Pro Met Gly Pro Ser Gly Pro Ala Gly Ala Arg Gly Ile
            595                 600                 605
Gln Gly Pro Gln Gly Pro Arg Gly Asp Lys Gly Glu Ala Gly Glu Pro
            610                 615                 620
Gly Glu Arg Gly Leu Lys Gly His Arg Gly Phe Thr Gly Leu Gln Gly
625                 630                 635                 640
Leu Pro Gly Pro Pro Gly Pro Ser Gly Asp Gln Gly Ala Ser Gly Pro
            645                 650                 655
Ala Gly Pro Ser Gly Pro Arg Gly Pro Pro Gly Pro Val Gly Pro Ser
            660                 665                 670
Gly Lys Asp Gly Ala Asn Gly Ile Pro Gly Pro Ile Gly Pro Pro Gly
            675                 680                 685
Pro Arg Gly Arg Ser Gly Glu Thr Gly Pro Ala Gly Pro Pro Gly Asn
            690                 695                 700
Pro Gly Pro Pro Gly Pro Pro Gly Pro Pro
705                 710
```

US 7,115,378 B2

PEPTIDE BIOMARKER AND METHOD OF IDENTIFICATION

STATEMENT REGARDING FEDERALLY SPONSORED RESEARCH OR DEVELOPMENT

This application claims priority to provisional application Ser. No. 60/316,554, filed Aug. 31, 2001.

FIELD OF INVENTION

The invention relates generally to methods for identifying and quantifying peptides and, more particularly, to a method for identifying and quantifying degradation peptides resulting from enzyme cleavage of collagen by collagenases. The invention also relates to the specific peptides that result from enzymatic cleavage of collagen type II in humans and animals and the recognition of these peptides as markers in biological samples of the activity of proteolytic enzymes, namely collagenases, in diseases or physiological conditions characterized by enzymatic degradation of collagen, such as osteoarthritis and rheumatoid arthritis, and the identification and quantification of the peptides to assess the efficacy of enzyme inhibiting agents and drugs used to treat or control such diseases or physiological conditions.

BACKGROUND OF THE INVENTION

Generally, active and extensive collagen turnover is not considered a prominent feature in healthy adults. Turnover of collagen type II, a component of articular collagen, generally occurs in diseases, such as rheumatoid arthritis, osteoarthritis or other diseases or physiological conditions in which collagen degradation is a factor.

The breakdown of collagen type II is believed to be initiated by specific members of the matrix metalloproteinase family of enzymes, the collagenases. Collagens are comprised of three peptide strands wound in a helix formation. For example, collagen type II is comprised of a triple helix of three identical peptide strands referred to as peptide alpha 1, collagen type II (SEQ ID NO: 44). When collagen is degraded or cleaved by a collagenase, the cleavage takes place at a specific intra-helical site leaving the peptides vulnerable to further degradation or cleavage. In any event, the initial cleavage results in the generation of collagen fragments having an end defined by the proteolytic cleavage. For example, collagenase degradation of collagen type II results in a peptide fragment having the C-terminal sequence ending with: GPXGPQG, where X is proline or hydroxyproline. Billinghurst et al described this primary collagenase cleavage site and developed antibodies reactive to both the carboxy-terminal and amino-terminal "neoepitopes" generated by cleavage of native human collagen type II. (*J. Clin.Invest.* 99:1534–1545 (1997)). Otterness et al have described production of a monoclonal antibody directed against this carboxy-terminal "neoepitope" (Matrix Biology 18: 331–341 (1999)).

U.S. Pat. No. 6,030,792 to Otterness et. al. discloses antibodies for detecting collagen fragments resulting from collagenase cleavage of type II collagen. Poole et al. U.S. Pat. No. 6,132,976 provides a method for evaluating cartilage degradation by immunoassay measurement of type II collagen cleavage. In any event, the prior art methods for the detection of collagen type II enzymatic cleavage by detecting the presence of peptide fragments only determine the presence of the target C-terminus portion and immediately adjacent peptide sequence using antibodies specific for these sequence regions.

SUMMARY OF THE INVENTION

One embodiment of the present invention comprises a method of detecting enzymatic proteolysis of a collagen, the method comprising identifying and quantifying a specific peptide proteolysis product of the collagen occurring in a biological sample or biological extract. In one embodiment, the collagen is type II collagen and the specific peptide has a C-terminus represented by Gly-Pro-Pro-Gly-Pro-Gln-Gly (SEQ ID NO: 1) and post-translational modifications thereof. In another embodiment, the collagen is type I collagen and the specific peptide has a C-terminus represented by Gly-Thr-Pro-Gly-Pro-Gln-Gly (SEQ ID NO: 12) and post-translational modifications thereof. In another embodiment, the collagen is type III collagen and the specific peptide has a C-terminus represented by Gly-Ala-Pro-Gly-Pro-Leu-Gly (SEQ ID NO: 13) and post-translational modifications thereof.

In a preferred embodiment, the enzymatic proteolysis of a collagen is the result of collagenase activity, illustratively matrix metalloproteinase-13.

The method permits rapid and highly accurate monitoring of changes in collagenase activity caused by a drug, particularly a drug directed against the collagenase.

In one embodiment, the method comprises identifying and quantifying more than one specific peptide occurring in the biological sample or biological extract. The biological sample is illustratively synovial fluid, whole blood, plasma or urine.

Another embodiment of the invention provides a method for identifying the amino acid sequence of a peptide resulting from protein degradation by a proteolytic enzyme.

Another embodiment of the invention includes a method of identifying and quantifying a peptide in a biological fluid sample or biological extract by tandem mass spectrometric analysis to determine the mass of the peptide, to identify a characteristic or diagnostic carboxy-terminal amino acid sequence of the peptide upon fragmentation, and to determine the N-terminal sequence of the peptide based on additional peptide fragment ions and the observed molecular weight of the intact peptide.

Another embodiment of the invention provides a method of detecting a peptide having the specific C-terminal sequence Gly-Pro-Pro-Gly-Pro-Gln-Gly (SEQ ID NO: 1) and post-translational modifications thereof in a biological fluid sample or biological extract by identifying fragment ions of the C-terminal sequence Gly-Pro-Pro-Gly-Pro-Gln-Gly (SEQ ID NO: 1) and post-translational modifications thereof having known mass to charge ratios.

Another embodiment of the invention provides a method of detecting a peptide having the specific C-terminal sequence Gly-Pro-Pro-Gly-Pro-Gln-Gly (SEQ ID NO: 1) and post-translational modifications thereof in a biological fluid sample or biological extract to confirm the presence of peptide fragments of collagen type II that have been cleaved by a collagenase enzyme.

Another embodiment of the invention provides a method of identification and quantification of peptide sequence Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2) or post-translational modifications thereof in a biological sample or biological extract.

Another embodiment of the invention is the identification and quantification of peptide sequence Lys-Gly-Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu- Pro-Gly-Asp-Asp-Gly-Pro-Ser-Gly-Ala-Glu-Gly-Pro-Pro-Gly-Pro-Gln-Gly (SEQ ID NO: 15), or post-translational modifications thereof in a biological sample or biological extract.

Another embodiment of the invention is the identification and quantification of peptide sequence Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 16), or post-translational modifications thereof in a biological sample or biological extract.

Another embodiment of the invention is the identification and quantification of peptide sequence Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 17), or post-translational modifications thereof in a biological sample or biological extract.

Another embodiment of the invention is identification and quantification of peptide sequence Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 3) and post-translational modifications thereof in a biological sample.

Another embodiment of the invention is identification and quantification of peptide sequence Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 34), or post-translational modifications thereof in a biological sample or biological extract.

Another embodiment of the invention is identification and quantification of peptide sequence Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 35), or post-translational modifications thereof in a biological sample or biological extract.

Another embodiment of the invention is identification and quantification of peptide sequence Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 36) or post-translational modifications thereof in a biological sample or biological extract.

Another embodiment of the invention is identification and quantification of peptide sequence Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 37) or post-translational modifications thereof in a biological sample or biological extract.

Another embodiment of the invention is identification and quantification of peptide sequence Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 38) or post-translational modifications thereof in a biological sample or biological extract.

Another embodiment of the invention is identification and quantification of peptide sequence Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 4) and its post-translational modifications thereof in a biological sample.

Another embodiment of the invention is identification and quantification of peptide sequence Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 18), or post-translational modifications thereof in a biological sample or biological extract.

Another embodiment of the invention is identification and quantification of peptide sequence Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 19), or post-translational modifications thereof in a biological sample or biological extract.

Another embodiment of the invention is identification and quantification of peptide sequence Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 20), or post-translational modifications thereof in a biological sample or biological extract.

Another embodiment of the invention is identification and quantification of peptide sequence Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 21), or post-translational modifications thereof in a biological sample or biological extract.

Another embodiment of the invention is identification and quantification of peptide sequence Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 22), or post-translational modifications thereof in a biological sample or biological extract.

Another embodiment of the invention is identification and quantification of peptide sequence Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 23), or post-translational modifications thereof in a biological sample or biological extract.

Another embodiment of the invention is identification and quantification of peptide sequence Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 24), or post-translational modifications thereof in a biological sample or biological extract.

Another embodiment of the invention is identification and quantification of peptide sequence Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 25), or post-translational modifications thereof in a biological sample or biological extract.

Another embodiment of the invention is identification and quantification of peptide sequence Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 26), or post-translational modifications thereof in a biological sample or biological extract.

Another embodiment of the invention is identification and quantification of peptide sequence Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 27), or post-translational modifications thereof in a biological sample or biological extract.

Another embodiment of the invention is identification and quantification of peptide sequence Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 28), or post-translational modifications thereof in a biological sample or biological extract.

Another embodiment of the invention is identification and quantification of peptide sequence Lys-Gly-Ala-Arg-Gly- Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 29), or post-translational modifications thereof in a biological sample or biological extract.

Another embodiment of the invention is identification and quantification of peptide sequence Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 11), or post-translational modifications thereof in a biological sample or biological extract.

Another embodiment of the invention is identification and quantification of peptide sequence Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 30), or post-translational modifications thereof in a biological sample or biological extract.

Another embodiment of the invention is identification and quantification of peptide sequence Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 31), or post-translational modifications thereof in a biological sample or biological extract.

Another embodiment of the invention is identification and quantification of peptide sequence Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 32), or post-translational modifications thereof in a biological sample or biological extract.

Another embodiment of the invention is identification and quantification of peptide sequence Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 33), or post-translational modifications thereof in a biological sample or biological extract.

Another embodiment of the invention is identification and quantification of peptide sequence Leu-Gln-Gly-Pro-Ala-Gly-Ala-Pro-Gly-Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 8), or post-translational modifications thereof in a biological sample or biological extract.

Another embodiment of the invention is identification and quantification of peptide sequence Ala-Pro-Gly-Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 39), or post-translational modifications thereof in a biological sample or biological extract.

Another embodiment of the invention is identification and quantification of peptide sequence Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 40), or post-translational modifications thereof in a biological sample or biological extract.

Another embodiment of the invention is identification and quantification of peptide sequence Gly-Glu-Pro-Gly-Asp-Asp-Gly-Pro-Ser-Gly-Ser-Asp-Gly-Pro-Pro-Gly-Pro-Gln-Gly (SEQ ID NO: 41), or post-translational modifications thereof in a biological sample or biological extract.

Another embodiment of the invention is identification and quantification of peptide sequence Asp-Gly-Pro-Ser-Gly-Ser-Asp-Gly-Pro-Pro-Gly-Pro-Gln-Gly (SEQ ID NO: 42), or post-translational modifications thereof in a biological sample or biological extract.

Another embodiment of the invention is identification and quantification of peptide sequence Val-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Val-Ser-Gly-Ala-Asp-Gly-Pro-Pro-Gly-Pro-Gln-Gly (SEQ ID NO: 43), or post-translational modifications thereof in a biological sample or biological extract.

Another embodiment of the invention is the identification and quantification of SEQ ID NO: 2, peptide SEQ ID NO: 3, or peptide SEQ ID NO: 4 in a biological sample as a marker of proteolytic enzyme activity.

Another embodiment of the invention is the identification and quantification of peptide SEQ ID NO: 8, peptide SEQ ID NO: 11, peptide SEQ ID NO: 15, peptide SEQ ID NO: 16, peptide SEQ ID NO: 17, peptide SEQ ID NO: 18, peptide SEQ ID NO: 19, peptide SEQ ID NO: 20, peptide SEQ ID NO: 21, peptide SEQ ID NO: 22, peptide SEQ ID NO: 23, peptide SEQ ID NO: 24, peptide SEQ ID NO: 25, peptide SEQ ID NO: 26, peptide SEQ ID NO: 27, peptide SEQ ID NO: 28, peptide SEQ ID NO: 29, peptide SEQ ID NO: 30, peptide SEQ ID NO: 31, peptide SEQ ID NO: 32, peptide SEQ ID NO: 33, peptide SEQ ID NO: 34, peptide SEQ ID NO: 35, peptide SEQ ID NO: 36, peptide SEQ ID NO: 37, peptide SEQ ID NO: 38, peptide SEQ ID NO: 39, peptide SEQ ID NO: 40, peptide SEQ ID NO: 41, peptide SEQ ID NO: 42 and SEQ ID NO: 43 in a biological sample as a marker of proteolytic enzyme activity.

Another embodiment of the invention is the identification and quantification of peptide SEQ ID NO: 2, peptide SEQ ID NO: 3, or peptide SEQ ID NO: 4 in a biological sample as a marker of the presence of a disease or physiological condition in subjects characterized by the degradation of collagen type II; such disease or physiological conditions include, but are not limited to osteoarthritis and rheumatoid arthritis.

Another embodiment of the invention is the identification and quantification of peptide SEQ ID NO: 8, peptide SEQ ID NO: 11, peptide SEQ ID NO: 15, peptide SEQ ID NO: 16, peptide SEQ ID NO: 17, peptide SEQ ID NO: 18, peptide SEQ ID NO: 19, peptide SEQ ID NO: 20, peptide SEQ ID NO: 21, peptide SEQ ID NO: 22, peptide SEQ ID NO: 23, peptide SEQ ID NO: 24, peptide SEQ ID NO: 25, peptide SEQ ID NO: 26, peptide SEQ ID NO: 27, peptide SEQ ID NO: 28, peptide SEQ ID NO: 29, peptide SEQ ID NO: 30, peptide SEQ ID NO: 31, peptide SEQ ID NO: 32, peptide SEQ ID NO: 33, peptide SEQ ID NO: 34, peptide SEQ ID NO: 35, peptide SEQ ID NO: 36, peptide SEQ ID NO: 37, peptide SEQ ID NO: 38, peptide SEQ ID NO: 39, peptide SEQ ID NO: 40, peptide SEQ ID NO: 41, peptide SEQ ID NO: 42 and SEQ ID NO: 43 in a biological sample as a marker of the presence of a disease or physiological condition in subjects characterized by the degradation of collagen type II, such disease or physiological conditions include, but are not limited to osteoarthritis and rheumatoid arthritis.

Another embodiment of the invention is identification and quantification of peptide SEQ ID NO: 2, peptide SEQ ID NO: 3 or peptide SEQ ID NO: 4 in a biological sample to evaluate or monitor the effectiveness of drugs or agents used to treat or control a disease or physiological condition characterized by proteolytic degradation of collagen.

Another embodiment of the invention is identification and quantification of the peptide SEQ ID NO: 8, peptide SEQ ID NO: 11, peptide SEQ ID NO: 15, peptide SEQ ID NO: 16, peptide SEQ ID NO: 17, peptide SEQ ID NO: 18, peptide SEQ ID NO: 19, peptide SEQ ID NO: 20, peptide SEQ ID NO: 21, peptide SEQ ID NO: 22, peptide SEQ ID NO: 23, peptide SEQ ID NO: 24, peptide SEQ ID NO: 25, peptide SEQ ID NO: 26, peptide SEQ ID NO: 27, peptide SEQ ID NO: 28, peptide SEQ ID NO: 29, peptide SEQ ID NO: 30, peptide SEQ ID NO: 31, peptide SEQ ID NO: 32, peptide SEQ ID NO: 33, peptide SEQ ID NO: 34, peptide SEQ ID NO: 35, peptide SEQ ID NO: 36, peptide SEQ ID NO: 37, peptide SEQ ID NO: 38, peptide SEQ ID NO: 39, peptide SEQ ID NO: 40, peptide SEQ ID NO: 41, peptide SEQ ID NO: 42 and SEQ ID NO: 43 in a biological sample to evaluate or monitor the effectiveness of drugs or agents used to treat or control a disease or physiological condition characterized by proteolytic degradation of collagen.

These and other objects, advantages and features of the invention will become apparent to those persons skilled in the art upon reading the details of the methods and the peptides fully described below.

DETAILED DESCRIPTION OF THE INVENTION

Figure 1:
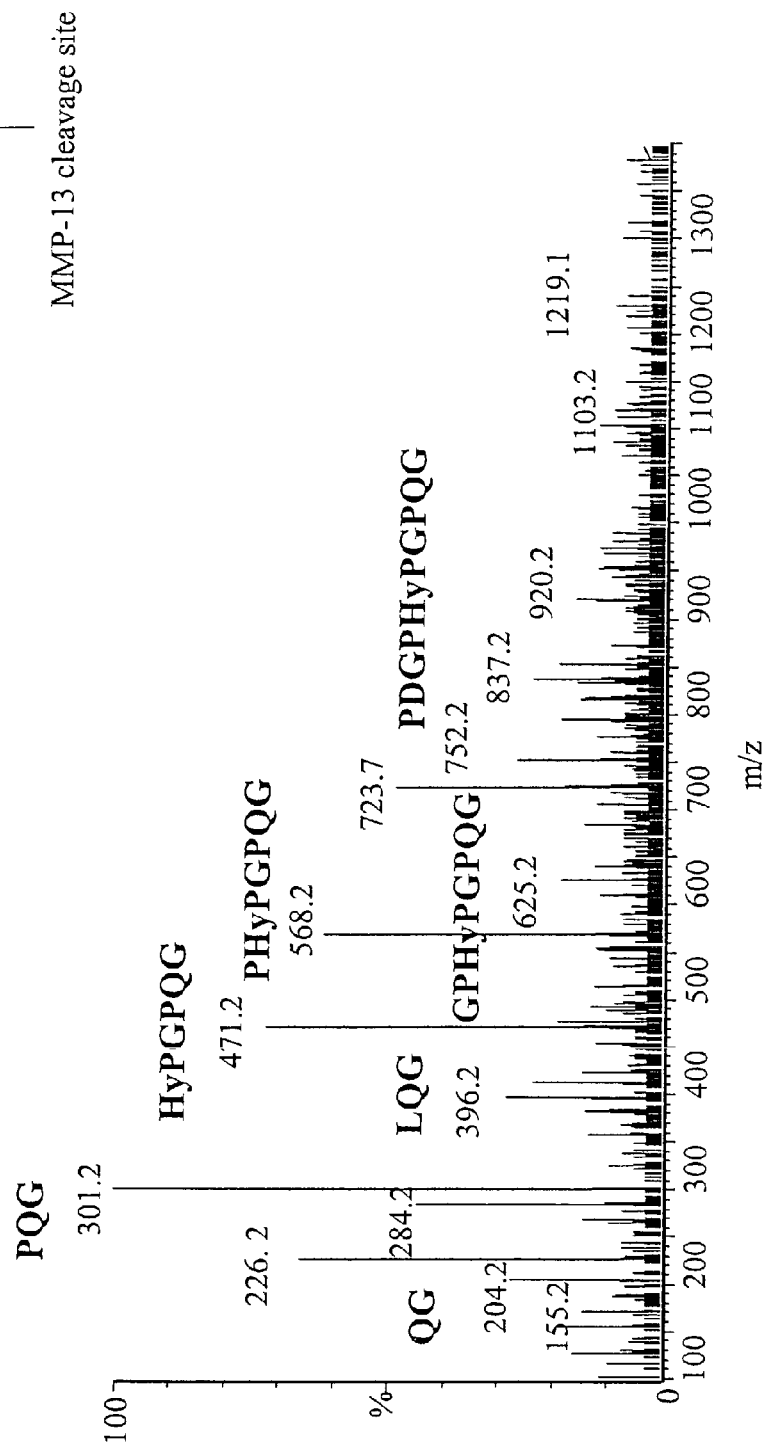
FIG. 1 illustrates the fragment ions of peptide SEQ ID NO: 3, having a C-terminal sequence (SEQ ID NO: 1) produced by tandem mass spectrometric analysis of urine from a bovine subject exhibiting signs and symptoms of arthritis.

One embodiment of the invention is directed to the identification and quantification of collagen peptides, particularly in biological samples from humans or animals. The term "biological sample" includes a sample from any body fluid or tissue. The invention includes a method of determining the presence of, and identifying the structure of, peptide degradation products of specific collagenase enzyme activity.

The present invention can be used to detect cleavage by proteolytic enzymes, such as matrix metalloproteinases-1, -8, and -13, that results in peptides with C-terminal amino acid sequences having characteristic fragment ions upon collisional activation by tandem mass spectrometry that can be identified by the methods of the present invention. The present invention allows the diagnosis and prognosis of physiological conditions characterized by cartilage degradation through the identification and quantification of collagen degradation peptides discovered to be present in biological samples of subjects exhibiting signs and symptoms of diseases characterized by cartilage degradation, such as osteoarthritis and rheumatoid arthritis. The invention is particularly useful in that it allows the detection and quantification of post-translational analogs of the peptides. The present invention also includes those newly discovered peptides and the post-translational analogs thereof.

One method of the invention relates to mass spectrometric analysis of peptide fragments in biological fluid samples or biological extracts to detect and measure protein degradation products, particularly proteins degraded by proteolytic enzymes. The proteolytic enzyme cleavage of a protein yields degradation peptides having a characteristic C-terminal amino sequence, depending upon the species, the source of the protein, and the involved enzyme. In one embodiment of the invention collagen degradation peptides of a known mass in a biological sample are separated by chromatographic techniques and then fragmented by collisional activation in the mass spectrometer using techniques known in the art. Upon collisional activation, the peptides yield fragments having characteristic mass to charge ratios. By detecting the presence of the characteristic peptide fragments of the C-terminus, for example, the sequence of the C-terminus is confirmed. Confirming the C-terminus sequence and the mass of the degradation peptide allows the deduction of the N-terminus of the peptide.

The peptide and fragment ion molecular weights determined in the tandem mass spectrum of the peptide are compared to those expected from known protein sequences, with postulated post-translational modifications, found in a protein database to determine the entire amino acid sequence including post-translational modifications of the peptide. The identification methods of the present invention allow identification of the C-terminal and the N-terminal sequences and, therefore, the amino acid sequence of the entire degradation peptide, including potential hydroxylation of proline amino acids present in the peptide. The peptide identity is further validated by synthesizing the peptide and demonstrating that the synthetic peptide provides the same analytical data, including liquid chromatographic elution time and mass spectrometric fragmentation as the peptide identified from biological sample. Once the peptide is identified, a standard peptide with the same or similar sequence can be used to determine the relative amount of the enzymatically cleaved peptide in the biological sample. This quantification can be used to assess proteolytic enzyme activity, for diagnosis or prognosis of diseases, and to evaluate drugs or agents used to modify proteolytic enzyme activity.

One embodiment of the invention provides for the identification and quantification of collagen cleavage products. For example, one embodiment of the invention provides for the identification and quantification of collagen types I, II and III breakdown products. A preferred embodiment of the present invention provides detection and quantification of specific, newly discovered protein cleavage products of collagen type II in a biological sample. The invention can be used to detect the presence of proteolytic enzyme degradation products resulting from the degradation of collagen type II by enzymes, such as matrix metalloproteinases, particularly matrix metalloproteinases-1, -8, and -13.

Identification and quantification of collagen type II peptide fragments in urine samples of humans initially indicated that post-translationally modified analog peptides of Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2), where in the most abundant form position 14 and 26 are 4-hydroxyproline, are present in detectable amounts in human subjects medically diagnosed with and displaying signs and symptoms of arthritis. The following peptides are also present in detectable amounts in human subjects medically diagnosed with and displaying signs and symptoms of arthritis: Lys-Gly-Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 15), where in the most abundant form positions 10, 16, 25, 31 and 42 are 4-hydroxyproline; Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 16), where in the most abundant form positions 8, 14, 23, 29 and 41 are 4-hydroxyproline; and Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 17), where in the most abundant form positions 12 and 24 are 4-hydroxyproline.

Peptide SEQ If) NO: 16 has been found to be the most abundant collagen II neoepitope peptide measured in human urine. In addition to the form in which five prolines are hydroxylated, as noted above, forms with four hydroxylated prolines and with five hydroxylated prolines and a hydroxylated lysine at position 26 are also common.

Identification of collagen type II peptide fragments in urine samples of cattle initially indicated that post-translationally modified analog peptides of Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 3), where in the most abundant form position 14 and 26 are 4-hydroxyproline, are present in detectable amounts in bovine subjects displaying signs and symptoms of arthritis. The following peptides also are present in detectable amounts in bovine subjects displaying signs and symptoms of arthritis. : Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 34), where in the most abundant form positions 10, 16, 25, 28, and 43 are 4-hydroxyproline and position 43 is hydroxylysine; and Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 35), where in the most abundant form positions 8,14,23,29 and 41 are 4-hydroxyproline and position 26 is hydroxylysine. Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 36), where in the most abundant form positions 4, 10 and 22 are 4-hydroxyproline and position 7 is hydroxylysine; Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 37), where in the most abundant form positions 4, 8 and 20 are 4-hydroxyproline and position 5 is hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 38), where in the most abundant form positions 2 is hydroxylysine and positions 5 and 17 are 4-hydroxyproline.

Peptide SEQ ID NO: 35 is the most abundant collagen II neoepitope peptide measured in bovine urine Likewise, identification and quantification of collagen type II peptide fragments in urine samples of dogs indicated post-translationally-modified analog peptides of Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 4), where in the most abundant form position 14 or 26 is 4-hydroxyproline, are present in detectable amounts in canine subjects displaying signs and symptoms of arthritis. The following peptides also are found in detectable amounts in canine subjects displaying signs and symptoms of arthritis: Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 18), where in the most abundant form positions 10, 16, 25, 31 and 43 are 4-hydroxyproline and position 28 is hydroxylysine; Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 19), where in the most abundant form positions 8, 14, 23, 29, and 41 are 4-hydroxyproline and position 26 is hydroxylysine; Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 20), where in the most abundant form positions 4, 10 and 22 are 4-hydroxyproline and position 10 is hydroxylysine; Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 21), where in the most abundant form positions 2, 8 and 20 are 2-, 3- or 4-hydroxyproline and position and position 5 is 4-hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 22), where in the most abundant form position 2 is hydroxylysine and positions 5 and 17 are 4-hydroxyproline.

Peptide SEQ ID NO: 19 is the most abundant collagen II neoepitope peptide measured in canine urine.

The following are the most abundant peptides found in urine of cats exhibiting signs and sysmptoms of arthritis: Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 23), where in the most abundant form positions 10, 16, 25, 31 and 43 are 4-hydroxyproline and position 28 is hydroxylysine;

Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 24), where in the most abundant form positions 8, 14, 23, 29 and 41 are 4-hydroxyproline and position 26 is hydroxylysine; Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Leu-Gln-Gly-Pro-Pro-Gly-Pro-Gln-Gly (SEQ ID NO: 25), where in the most abundant form positions 8, 14 and 26 are 4-hydroxyproline and position 11 is -hydroxylysine; Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 26), where in the most abundant form positions 4, 10 and 22 are 4-hydroxyproline and position 7 is hydroxylysine; Pro-Pro-Gly-Glu-Lys-Gly-Glu-Pro-Gly-Asp-Asp-Gly-Pro-Ser-Leu-Gln-Gly-Pro-Gly-Pro-Asp-Gly-Pro-Pro-Gly-Pro-Gln-Gly (SEQ ID NO: 27), where in the most abundant form positions 2, 8, and 20 are 4-hydroxyproline and position 5 is hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 28), where in the most abundant form position 2 is hydroxylysine and positions 5 and 17 are 4-hydroxyproline.

Peptide SEQ ID NO: 24 is the most abundant peptide neoepitope found in urine of feline subjects.

The following are the most abundant collagen II peptides found in the urine of horses exhibiting signs and symptoms of arthritis: Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 11), where in the most abundant form positions 8, 14 and 26 are 4-hydroxyproline and position 11 is hydroxylysine, Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 29), where in the most abundant form positions 10, 16, 25, 31 and 43 are 4-hydroxyproline and position 28 is -hydroxylysine; Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 30), where in the most abundant form positions 8, 14, 23, 29 and 41 are 4-hydroxyproline and position 26 is hydroxylysine; Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 31), where in the most abundant form positions 4, 10 and 22 are 4-hydroxyproline and position 7 is hydroxylysine; Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 32), where in the most abundant form positions 2, 8, and 20 are 4-hydroxyproline and positions 26 is hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 33), where in the most abundant form position 2 is hydroxylysine and positions 5 and 17 are 4-hydroxyproline.

Peptide SEQ ID NO: 30 is the most abundant collagen II neoepitope peptide found in equine urine.

The following are the most abundant collagen type II peptides found in urine of adjuvant arthritic rat subjects: Leu-Gln-Gly-Pro-Ala-Gly-Ala-Pro-Gly-Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 8), where in the most abundant form positions 8, 14 and 26 are 4-hydroxyproline and position 11 is hydroxylysine; Ala-Pro-Gly-Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 39), where in the most abundant form positions 2, 8 and 20 are 4-hydroxyproline and position 5 is hydroxylysine; Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 40), where in the most abundant form position 2 is hydroxylysine and positions 5 and 17 are 4-hydroxyproline; Gly-Glu-Pro-Gly-Asp-Asp-Gly-Pro-Ser-Gly-Ser-Asp-Gly-Pro-Pro-Gly-Pro-Gln-Gly (SEQ ID NO: 41), where in the most abundant form positions 3 and 15 are 4-hydroxyprolines; and Asp-Gly-Pro-Ser-Gly-Ser-Asp-Gly-Pro-Pro-Gly-Pro-Gln-Gly (SEQ ID NO: 42), wherein position 10 is 4-hydroxyproline.

Peptide SEQ ID NO: 42 is the most abundant collagen II neoepitope peptide measured in rat urine.

The following is an abundant collagen type II peptide found in urine of cavia porcellus (guinea pig) subject exhibiting signs and symptoms of arthritis: Val-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Val-Ser-Gly-Ala-Asp-Gly-Pro-Pro-Gly-Pro-Gln-Gly (SEQ ID NO: 43), where in the most abundant form positions 8, 14, 23, 20 and 41 are 4-hydroxyprolines and position 26 is hydroxylysine.

It is noted that the post-translational modifications, 4-hydroxylation of proline and hydroxylation of lysine, appear in varying levels in different species. The originally translated peptides themselves, as well as permutations of the post-translational modifications, may be found in urine of subjects and are included among the embodiments of the invention.

It is believed these degradation peptides are a result of cleavage of collagen type II by collagenase, particularly matrix metalloproteinases, and more particularly matrix metalloproteinase-13 (MMP-13). Thus, the peptides SEQ ID NO: 2, SEQ ID NO: 3, SEQ ID NO: 4, SEQ ID NO: 8, SEQ ID NO: 11, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 and particularly the post-translational analogs thereof, found in biological samples function as markers of enzyme activity and/or markers of diseases or conditions characterized by collagen type II breakdown, such as osteoarthritis and rheumatoid arthritis. Identifiable derivatives or modifications of the peptides also can function as markers and are included within the scope of the invention.

The identification and quantification of the peptides SEQ ID NO: 2, SEQ ID NO: 3 or SEQ ID NO: 4, SEQ ID NO: 8, SEQ ID NO: 11, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43 and their post-translationally modified analog peptides, in general, is performed by the following illustrative analytical detection method:

A biological sample, such as urine, plasma, blood or synovial fluid is collected from the subject.

The relative molecular mass of peptides in the sample is determined by a first stage mass spectrometry and then the peptides are fragmented and fragment ions analyzed by second stage of the tandem mass spectrometer, as will be further explained below. As way of example, the post-translational analogs of peptides SEQ ID NO: 2, SEQ ID NO: 3 and SEQ ID NO: 4 found in picomolar to nanomolar amounts in the biological samples of subjects exhibiting signs and symptoms of arthritis have a mass/charge ratio in the range of approximately 900 to approximately 1000 with known variations of the mass/charge ratio within this range depending upon the post-translational modifications of proline and in some examples, lysine. The charge for these peptides is +3. As will be discussed more specifically in the examples below, the relative mass/charge of the abundant post-translation analog of peptide SEQ ID NO: 2 was determined to be 914.4 and the charge was +3. The mass/charge of the abundant post-translation analog of peptide SEQ ID NO: 3 was shown to be 918.7 and, the relative mass/charge of the abundant post-translation analog of peptide SEQ ID NO: 4 was shown to be 913.4, as described in the examples below.

The peptides can be separated from the biological matrix components of the sample by an appropriate separation method known to the art. For example, chromatographic or electrophoretic separation can be used in this step. Other appropriate separation or "clean up" methods are contemplated by the invention. In liquid chromatographic separation the eluant containing the peptides of the target mass are introduced to a mass spectrometer through an appropriate liquid chromatography/mass spectrometry interface.

The peptides are fragmented by collisional activation by a neutral gas in a collision cell using collision energies and methods known to the art resulting in collision-induced dissociation of the peptide to create corresponding fragment ions. The spectrum of the fragment ions is analyzed. Peptides having the C-terminal sequence Gly-Pro-Pro-Gly-Pro-Gln-Gly (SEQ ID NO: 1), where proline at the third position may be in the post-translationally modified form, hydroxyproline, fragment to yield product ions having characteristic mass to charge ratios. As demonstrated, where the proline at position 3 of SEQ ID NO: 1 is 4-hydroxyproline, the respective masses of the characteristic fragments are approximately m/z 301, 471 and 568. These characteristic fragments of C-terminal sequences are a result of the dominant cleavage of the peptide bonds on the N-terminal side of proline. The peptides having a C-terminus of Gly-Pro-Pro-Gly-Pro-Gln-Gly (SEQ ID NO: 1), i.e., the non-modified form, will fragment to form fragment ions of the sequence Pro-Gln-Gly (SEQ ID NO: 5) having a mass of approximately 301, sequence Pro-Gly-Pro-Gln-Gly (SEQ ID NO: 6) having a mass of approximately 455 and sequence Pro-Pro-Gly-Pro-Gln-Gly (SEQ ID NO: 7) having a mass of approximately 552.

Identification of the characteristic product ions is a strong indication of the presence of the C-terminal sequence Gly-Pro-Pro-Gly-Pro-Gln-Gly (SEQ ID NO: 1) or post-translation modifications thereof. Consequently, peptides SEQ ID NO: 5, SEQ ID NO: 6, and SEQ ID NO: 7 also are markers of collagen II degradation in their own right.

As described below, through further identification of peptide fragments in biological samples it was discovered that in human subjects medically diagnosed and exhibiting arthritic signs and symptoms, the predominant degradation peptides are the post-translational modifications of Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2), where prolines at positions 14 and 26 are 4-hydroxyproline and Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 16), where in the most abundant form positions 8, 14, 23, 29 and 41 are 4-hydroxyproline; Peptide SEQ ID NO: 16 being the more abundant of the two.

The post-translationally-modified peptides SEQ ID NO: 3 and SEQ ID NO: 19 were discovered to be the most abundant in dogs, with peptide SEQ ID NO: 19 being more abundant. The post-translationally-modified peptides SEQ ID NO: 4 and SEQ ID NO: 35 were discovered to be the predominant degradation peptides in cattle, with peptide SEQ ID NO: 35 being more abundant. The post-translationally-modified peptide SEQ ID NO: 24 was discovered to be the most abundant peptide found in cats; the post-translationally-modified peptide SEQ ID NO: 30 was discovered to be the most abundant peptide found in horses; the post-translationally-modified peptide SEQ ID NO. 42 was discovered to be the most abundant peptide found in rats; and the post-translationally-modified peptide SEQ ID NO: 42 was found to be the most abundant peptide found in guinea pigs, all which also exhibited signs and symptoms of cartilage degradation or arthritis.

Although these specifically recited peptides have been found to be most predominant in the sample taken from a recited species of animal and may serve as the more preferable biomarkers, all the discovered peptides sequences recited herein have utility as well, as discussed below.

It will be noted that when any proteolytic enzyme cleaves a protein or peptide, there is a resulting characteristic C-terminus, N-terminus, and potential post-translational modifications thereof. This is due to the fact that specific enzymes cleave proteins at specific sites in the amino acid sequence. Fragmentation of a peptide having a specific C-terminus will yield characteristic fragments upon collisional activation having specific mass to charge ratios. That is, upon fragmentation each C-terminus will have its own fingerprint. Consequently, the described method can be used to determine the amino acid sequence of any peptide that results from proteolytic cleavage leaving a known C-terminus that fragments into characteristic product ions.

The method of the present invention is not limited to identification and quantification of peptides resulting from the degradation of type II collagen or the specific peptides described herein by sequence identification numbers. The analytical methods of the present invention can be used to detect the presence of proteolytic enzyme degradation products resulting from the degradation of proteins other than the illustrated collagen type II or by enzymes other than collagenases, specifically, metalloproteinase-13 (MMP-13). By way of example only, the method of the present invention can be used to identify proteolytic degradation products resulting from cleavage by other matrix metalloproteinases such as matrix metalloproteinase-1 (MMP-1) and matrix metalloproteinase-8 (MMP-8).

Specific examples of how the method of the present invention was employed in the discovery of the described peptides follow:

EXAMPLE 1

Identification of a Bovine Collagen Type II Peptide Fragment

The following procedures were employed to determine that the post-translationally modified peptide of SEQ ID NO: 3 is present in the urine of cows exhibiting signs and symptoms of osteoarthritis:

Urine was collected from the subject identified as exhibiting the signs and symptoms of osteoarthritis pH of the urine was adjusted to 7.1 with ammonium acetate Sample was fractionated using a mixed-mode ion exchange reversed phase preparatory chromatography column Sample was eluted from the column Sample was evaporated to dryness Sample was reconstituted in an appropriate chromatography buffer Sample was analyzed by liquid chromatography-tandem mass spectrometry (LC-MS-MS) as follows:

Sample peptides were fragmented by collisional activation

Characteristic peptide fragments at m/z 301, 471, and 568 were identified as predominant fragments Peptides that fragmented to m/z 301, 471, and 568 were identified as post-translational modifications of Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 3), wherein the Pro at positions 14 and 26 are 4-hydroxyproline, as discussed below.

A fragmentation of a collagen type II peptide (SEQ ID NO: 3) having the Gly-Pro-Pro-Gly-Pro-Gln-Gly (SEQ ID NO: 1) C-terminus wherein the proline at position 3 is hydroxylated is illustrated in FIG. 1. The vertical (Y-axis) represents the fragment ion abundance (intensity) detected for a specific mass to charge ratio expressed as a percent of the total ions detected. The horizontal (X-axis) represents the mass to charge ratio of the detected fragment ions. The predominant fragmentation products of the peptides in the urine sample were identified as m/z 301, 471, and 568.

Software was used to match the fragment ions in an MS/MS spectrum of the peptide to the theoretical sequence ions produced in silico by cleaving all proteins in a protein database at every peptide bond (no enzyme specificity). The software matched the observed and theoretical molecular weights of an intact peptide and its fragment ions based on expected cleavages of the peptide between each of the amino acids. The software was employed to match the observed data to all possible peptides derived from all the proteins in a global protein database of known mammalian proteins. The program determined that the peptide having the mass m/z 918.7 for 3+, which fragments to yield ions at m/z 301, 471, and 568 was the post-translational modification of Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 3), wherein the prolines at positions 14 and 26 are 4-hydroxyproline.

To prove that the software determined the correct peptide, a standard of the peptide was synthesized and its LC retention time and MS/MS spectrum was matched to that of the peptide found in urine. The analytical data matched.

EXAMPLE 2

Identification and Quantification of Human Collagen Type II Peptide Fragment

The procedures used in Example 1 were used to identify the presence of peptide SEQ ID NO: 2 in urine samples obtained from a human subject diagnosed with and exhibiting the signs and symptoms of osteoarthritis.

Figure 2:
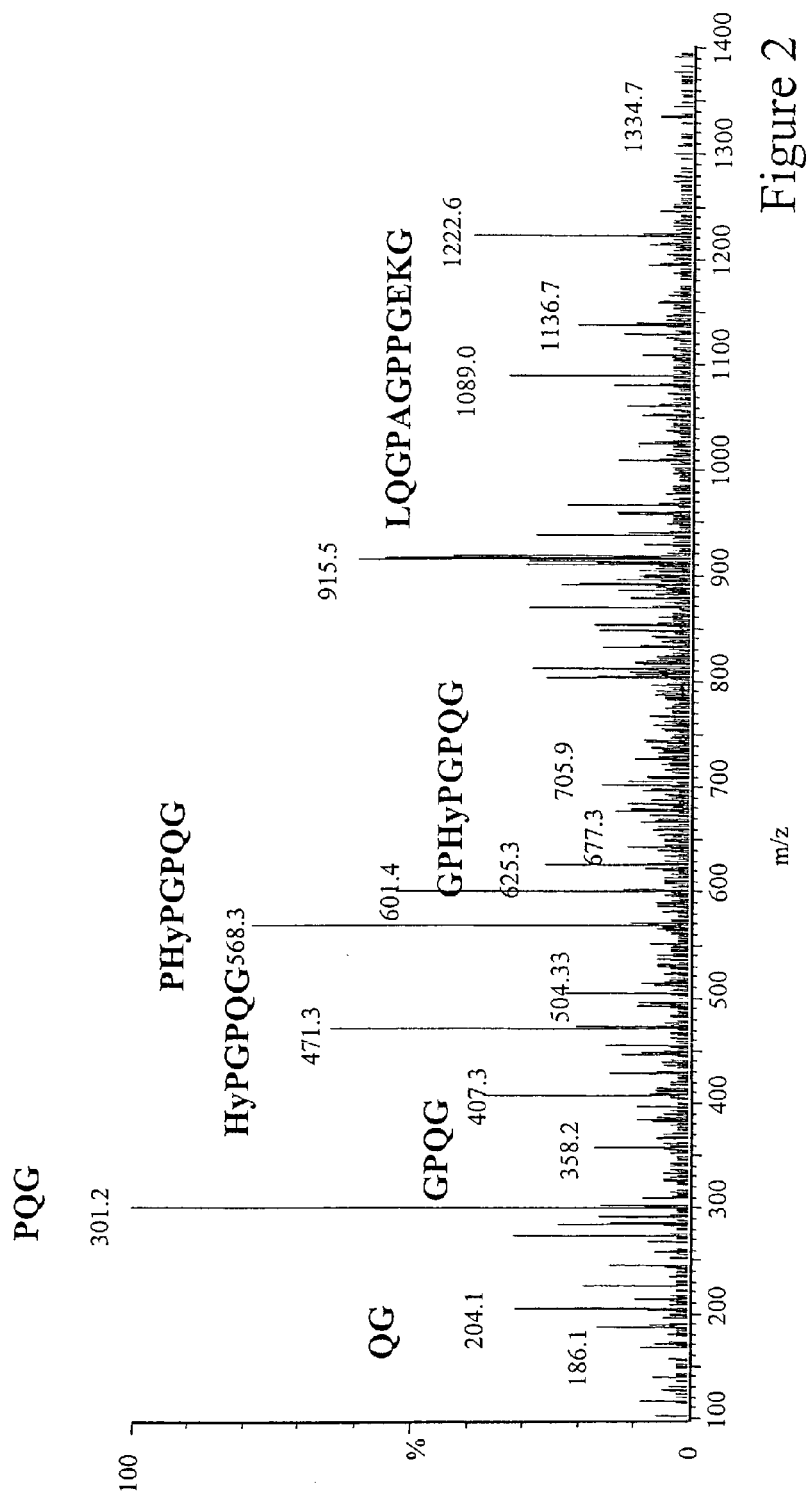
FIG. 2 illustrates the fragment ions of a peptide SEQ ID NO: 2, produced by tandem mass spectrometric analysis of urine from a human subject medically diagnosed with and exhibiting signs and symptoms of osteoarthritis.

FIG. 2 shows the fragmentation of a peptide in the sample from a human subject. As shown, the peptide is the post-translationally modified peptide Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2) wherein prolines at positions 14 and 26 are hydroxylated to 4-hydroxyproline. The peptide SEQ ID NO: 2 has the identified mass/charge of 914.4 with a charge of 3+. Fragmentation yielded the characteristic product ions of 301, 471, and 568 corresponding to SEQ. ID NO: 5, SEQ ID NO: 6, and SEQ ID NO: 7, respectively.

EXAMPLE 3

Identification and Quantification of Collagen Type II In Dog Urine Samples

The procedures used in Example 1 were used to identify the presence of peptide Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 4), wherein the proline at position 26 is 4-hydroxyproline in urine samples obtained from canine subjects diagnosed with, and exhibiting signs and symptoms of osteoarthritis.

Figure 3:
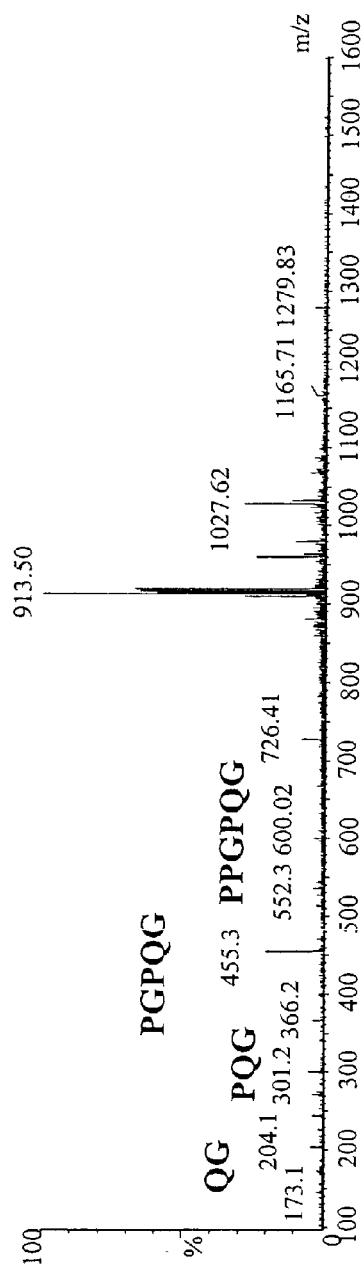
FIG. 3 illustrates the fragment ions of a peptide SEQ ID NO: 4, produced by tandem mass spectrometric analysis of urine from a canine subject exhibiting signs and symptoms of arthritis.
Figure 3:
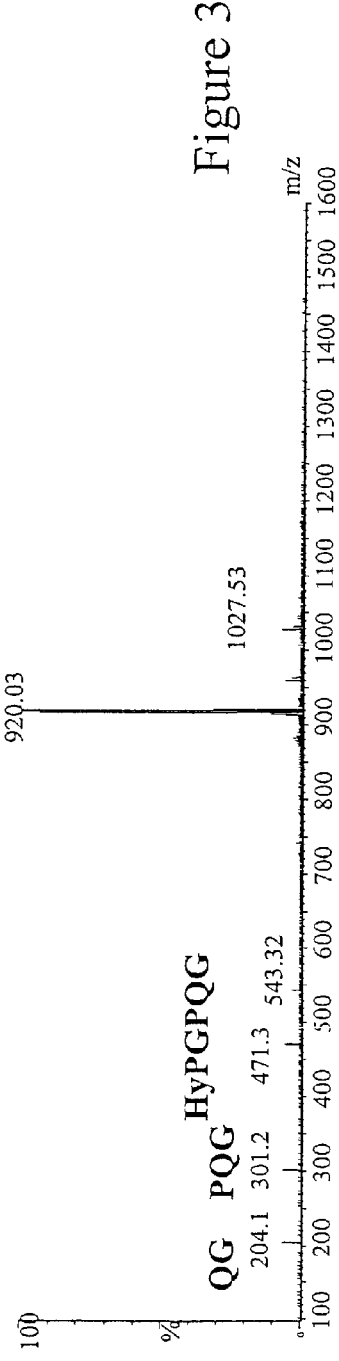

FIG. 3 shows the fragmentation of a peptide in the sample. As shown, the peptide is the post-translational modification of peptide Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 4), wherein the proline at position 14 or 26 is hydroxylated to 4-hydroxyproline. The peptide SEQ ID NO: 4 has the mass/charge of 913.4 with a charge of 3+. Fragmentation yielded the characteristic product ions at m/z 301, 471 or 455, and 568 or 552, corresponding to SEQ. ID NO: 5, SEQ ID NO: 6, and SEQ ID NO: 7, respectively. The same peptide sequence is present in at least two post-translationally-modified forms in canine urine: one form where proline-14 is hydroxylated as shown in the top tandem mass spectrum and a second form where proline-26 is hydroxylated as shown in the bottom tandem mass spectrum;

Example 1 describes the discovery of the specific and predominant peptide fragment in urine derived from collagen type II degradation by proteolytic enzymes in cattle having the following amino acid sequence: Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 3), and particularly the post-translational modifications thereof. Example 2 describes the discovery of the specific and predominant peptide sequence Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2) in urine derived from collagen type II degradation by proteolytic enzymes in humans. Example 3 describes the discovery of a specific and predominant peptide fragment in urine derived from collagen type II degradation by proteolytic enzymes in dogs, which has the following amino acid sequence: Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 4) or post-translational modifications thereof. All three peptides can include modifications of proline to 4 hydroxyproline at positions 8, 14 and 26 and lysine to 4 hydroxylysine at position 11. It will be noted that independent of the species of animal, upon fragmentation the predominant peptide yielded fragment ions having mass to charge ratios of approximately 301, 471 and 568. Fragmentation of the originally transcribed peptide (without post-translational conversion of the proline at position 26 to 4-hydroxyproline) would yield characteristic fragment ions having mass to charge ratios of approximately 301, 455 and 552 and are included within the scope of the invention.

Other characteristic fragment ions may be diagnostic within a given species. By way of example, FIG. 1 indicates that characteristic fragment ions having mass to charge ratios of 396 and 1219 are produced upon fragmentation of peptide SEQ ID NO: 3, found in samples from cattle. Also, as an example, FIG. 2 indicates that fragment ions having mass to charge ratios of 407 and 1222 are produced upon fragmentation of peptide SEQ ID NO: 2, found in samples from humans. Although the fragment ions having mass to charge ratios of approximately 301, 471 and 568 represent a preferred embodiment of the invention, other specific fragment ions may have utility when analyzing samples from that species and are included within the scope of the invention It was predicted that peptide SEQ ID NO: 11 and post-translational modifications would be found in specimens from horses, which was confirmed as set out in Example 10. It is predicted that peptide SEQ ID NO: 9 will be found in specimens from rabbits and SEQ ID NO: 10 will be found in specimens from mice; and as well as post-translational modifications of these peptides when these species exhibit signs and symptoms of collagen degradation, and likely even prior to manifestation of the signs and symptoms of arthritic disease.

Since it is now known that a specific peptide, for example, Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2), has been identified as a collagen type II degradation peptide in the biological fluid sample of humans, the relative quantity of that peptide in a given sample provides an indication of the extent of collagen II degradation occurring in the subject.

Figure 4:
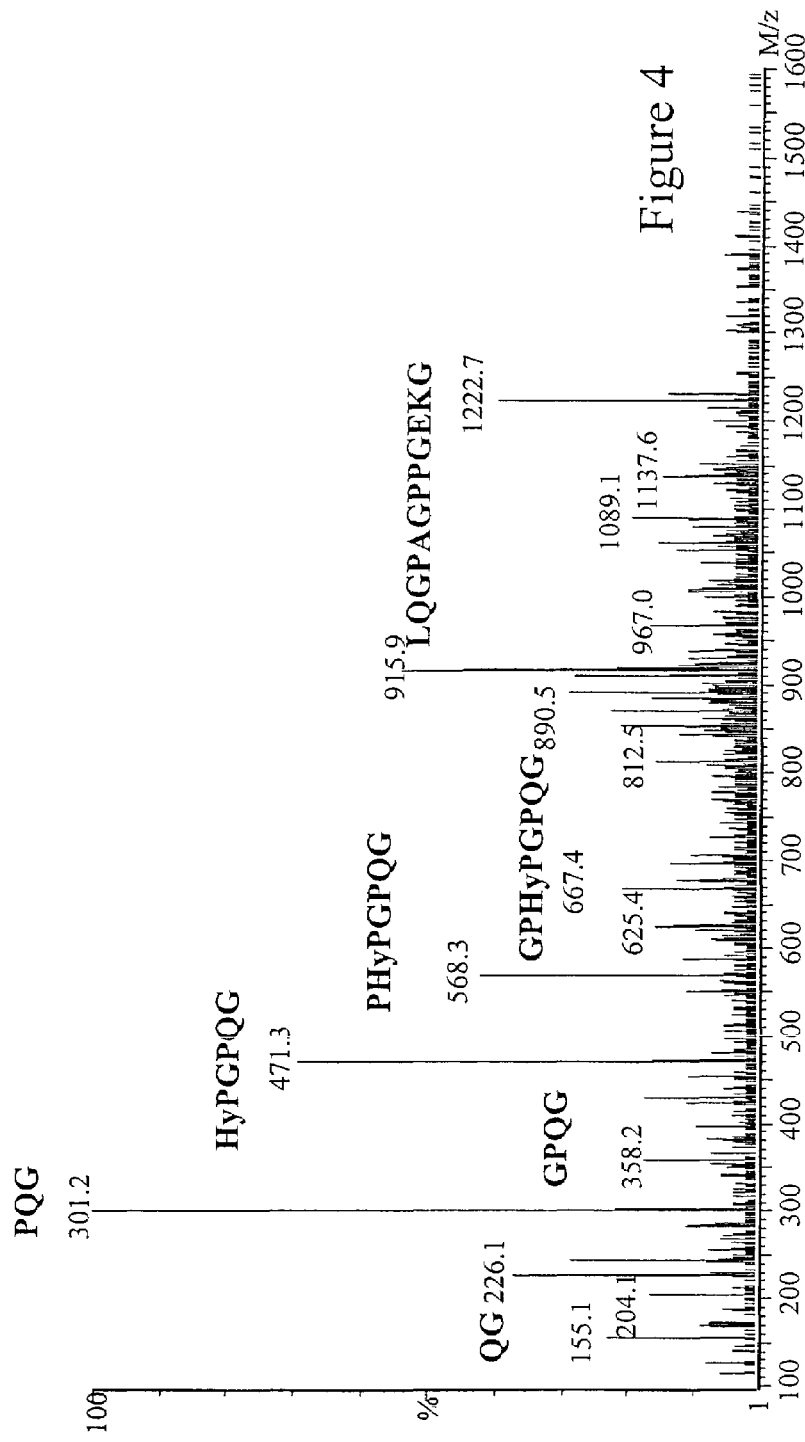
FIG. 4 illustrates the fragment ions of a human collagen type II synthetic peptide standard produced by tandem mass spectrometric analysis.
Figure 5:
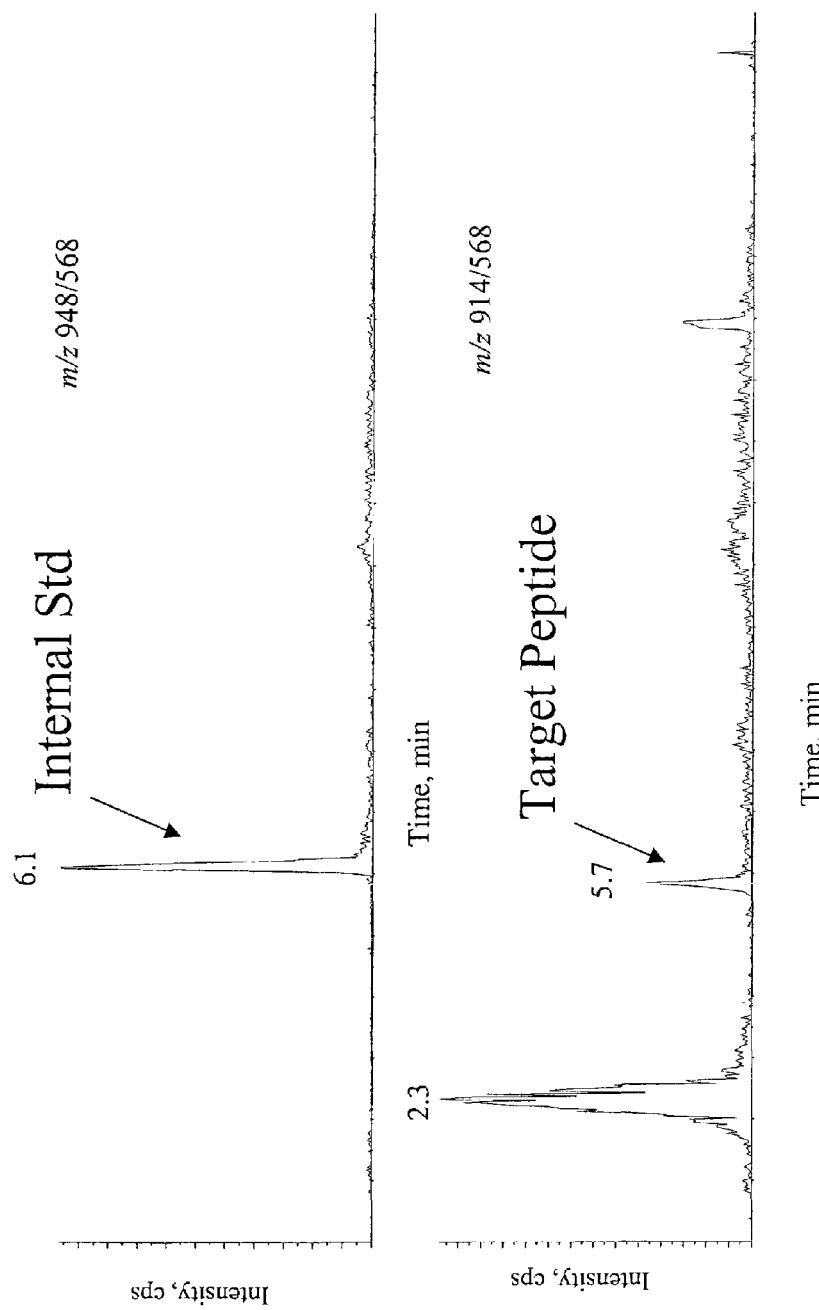
FIG. 5 shows the comparison of the extracted ion chromatograms for an internal standard peptide SEQ ID NO: 14 and collagen type II target peptide SEQ ID NO: 2, determined by tandem mass spectrometric quantification of the peptides in urine from a human subject medically diagnosed with, and exhibiting the signs and symptoms of osteoarthritis

The peptides SEQ ID NO: 2, SEQ ID NO: 3, or SEQ ID NO: 4 and likely SEQ ID NO: 9 and SEQ ID NO: 10, were identified and quantified by the following general, illustrative procedure:

A biological specimen, for example urine, is collected from the subject. The peptide, which can be referred to as the subject or target peptide, having the appropriate mass, for example m/z 918.7 for (M+3H)3+ (SEQ ID NO: 3) is extracted from the sample using procedures known to the art. See Example 4, below. The sample is spiked with a known quantity of a synthetic peptide (known as the internal standard) having a sequence very similar to the target peptide sequence. For example, peptide Val-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO. 14), may be used as an internal standard. Alternatively, stable-isotope labeled peptides with the identical sequence or compounds with dissimilar molecular structure may be spiked into the biological sample and used as an internal standards according to protocols known to the art. The sample is prepared and introduced to the LC-MS-MS for analysis. The presence of the target peptides is confirmed by three criteria: 1) it elutes from the LC column at the proper time, 2) it is the correct molecular weight, and, 3) upon collisional activation, yields the characteristic fragments of approximately m/z 301, 471 and 568 (shown in FIG. 4), or other known fragment ions of the peptide. FIG. 5 is a chromatogram showing the elution profile of the target peptide and an internal standard as a representative example. Comparison of the abundance of the target peptide (area under peak) to the abundance of a standard, normalized by the abundance of an internal standard indicates a relative quantity of target peptide in the sample. More particularly, the area under the curve representing the abundance of the standard peptide is compared to the area under the curve representing the abundance of the target peptide to obtain a relative quantity of target peptide in a sample. The areas of the standard and target peptides are normalized relative to the area of an internal standard peptide to adjust for sample-to-sample variability in extraction efficiency, detection, and other potential variables. Of course, acceptable methods of quantifying the target peptide in a biological sample are encompassed by the scope of the invention. A general quantitation procedure for collagen type II peptide biomarker in human urine is set out below in Example 4 as a representative procedure.

EXAMPLE 4

General Quantitation Procedure For Collagen Type II Peptide Biomarker In Human Urine 1. First pass urine is collected in polypropylene tubes. Samples are frozen at −80C until sample workup
2. 100 microliters of urine is aliquoted for creatinine quantitation, which is performed using standard procedures known in the art
3. Standard solutions ranging from 30 pg/mL to 100 ng/mL are prepared using a synthetic peptide standard
4. An internal standard (similar peptide) is spiked into 30 mL of each urine sample and standard to a final concentration of 1.0 nM
5. Urine solutions are extracted by mixed-phase (RP and AEX) preparatory chromatography:
   a. Equilibrate cartridge with 10 mL of MeOH
   b. Condition cartridge with 10 mL of 50 mM NH4OAc, pH 7
   c. Load Sample (pH 7)
   d. Wash with 10 mL of 50 mM NH4OAc, pH 7
   e. Wash with 10 mL 5% MeOH
   f Elute with 1 mL 5% Formic Acid, 95% MeOH
6. Eluant is evaporated to dryness and reconstituted in 100 microliters of 2% formic acid solution
7. Solutions are analyzed by LC/MS/MS
8. The collagen peptide in samples is quantified by correlating LC/MS/MS responses to those of the standards, normalized for the internal standard responses
9. Final peptide concentrations are normalized to creatinine levels Preparation of Standard Curve 1. Prepare Stock Solutions of Collagen II Peptide: 10 ng/mL, 100 ng/mL, 1 µg/mL, and 10 µg/mL.
2. Prepare Stock Solution of Internal Standard: 3 µg/mL
3. Add 100 µL of Internal Standard (3 µg/mL) to 30 mL of urine
4. Add 300 82 L of 10 ng/mL, 100 ng/mL, 1 µg/mL, and 10 µg/mL to 30 mL of urine to get 100 pg/mL, 1 ng/mL, 10 ng/mL, and 100 ng/mL standards, respectively. To get 30 pg/mL standard add 90 µL of 10 ng/mL stock solution to 30 mL of urine.

Figure 6:
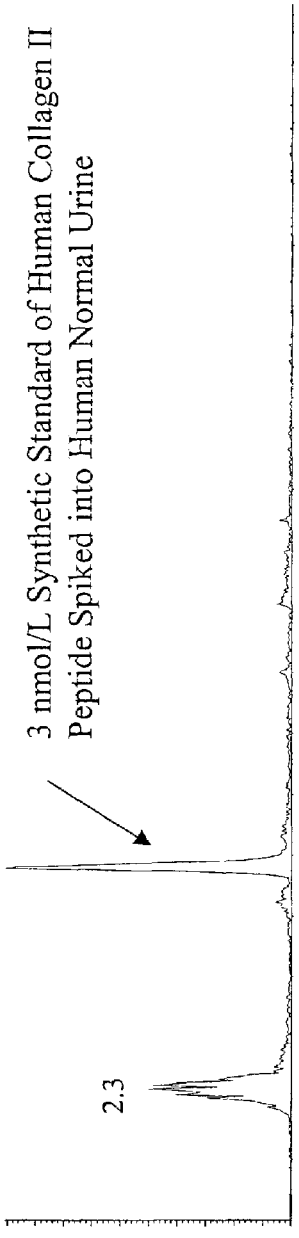
FIG. 6 is a comparison of the extracted ion chromatograms for the collagen type II target peptide SEQ ID NO: 2 determined by tandem mass spectrometric quantification of urine from a human subject that did not exhibit signs and symptoms of arthritis (bottom), from urine of a human subject that was medically diagnosed with and exhibited signs and symptoms of osteoarthritis (middle), and from urine of a human subject that did not exhibit signs and symptoms of arthritis that was spiked with a synthetic standard of the collagen II peptide.
Figure 6:
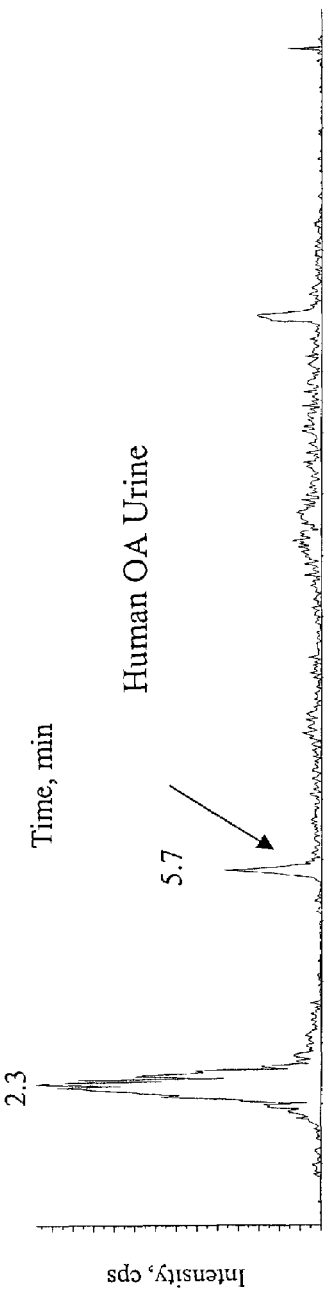
Figure 6:
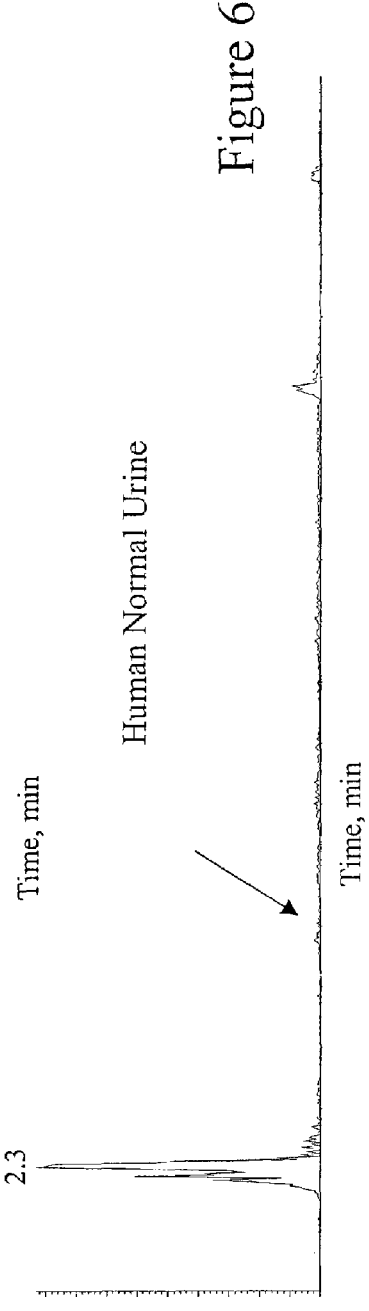
Figure 7:
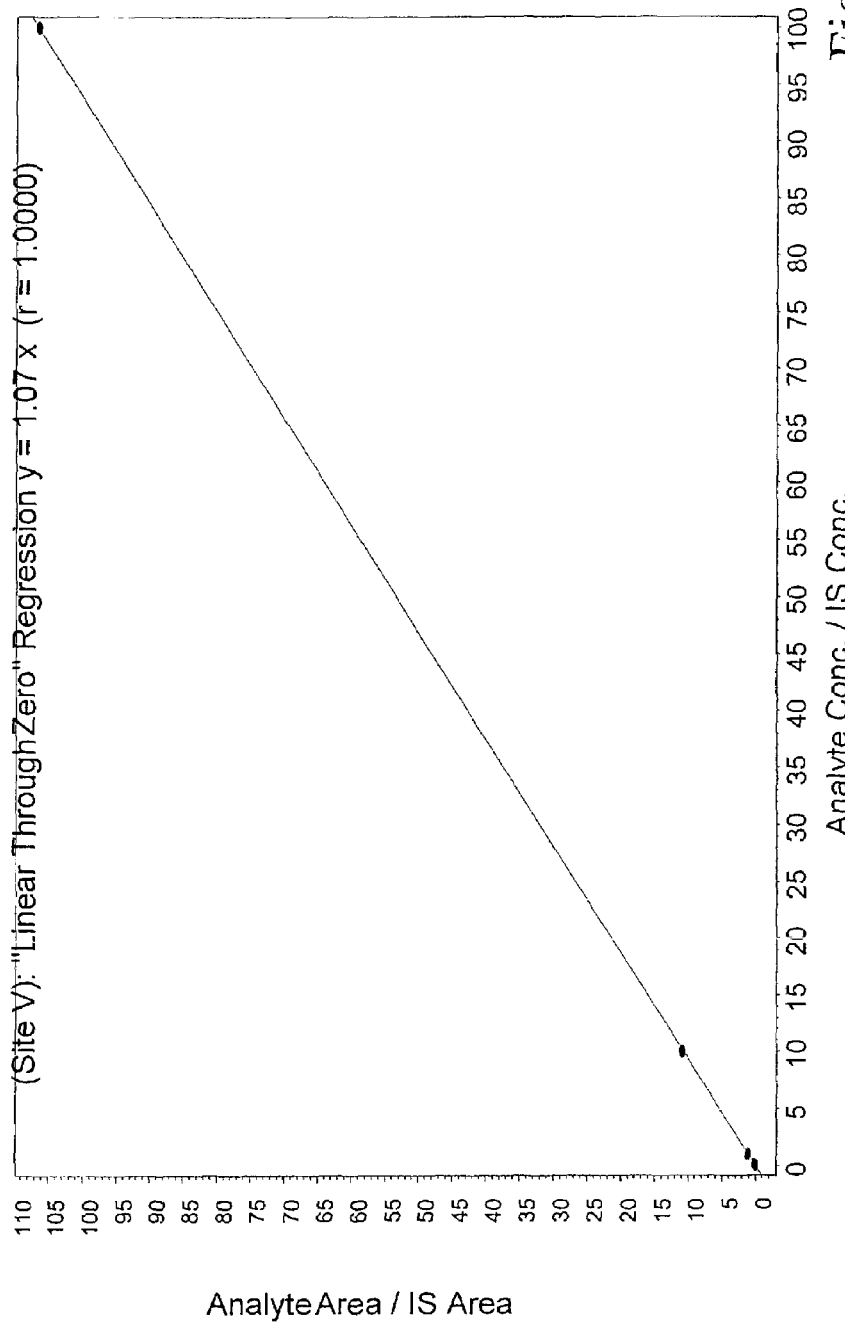
FIG. 7 shows the standard curve of the human collagen type II synthetic peptide spiked into normal human urine at concentrations ranging from 30 pg/mL to 100 ng/mL.

FIG. 6 graphically illustrates a comparison of extracted ion chromatograms for the 914/568 ion pair, which was used to measure the collagen type II peptide (SEQ ID NO: 2). The bottom scan shows that the peptide eluting at 5.7 minutes was not detected in human urine of a subject without signs and symptoms of arthritis. The middle scan shows detectable levels of the peptide, and the top scan shows that the synthetic analog of this peptide elutes at the same time. FIG. 7 illustrates a standard curve of the collagen type II peptide spiked into control human urine at various concentrations ranging from 30 pg/mL to 100 ng/mL. The response is linear over this concentration range for accurate quantification.

Figure 8:
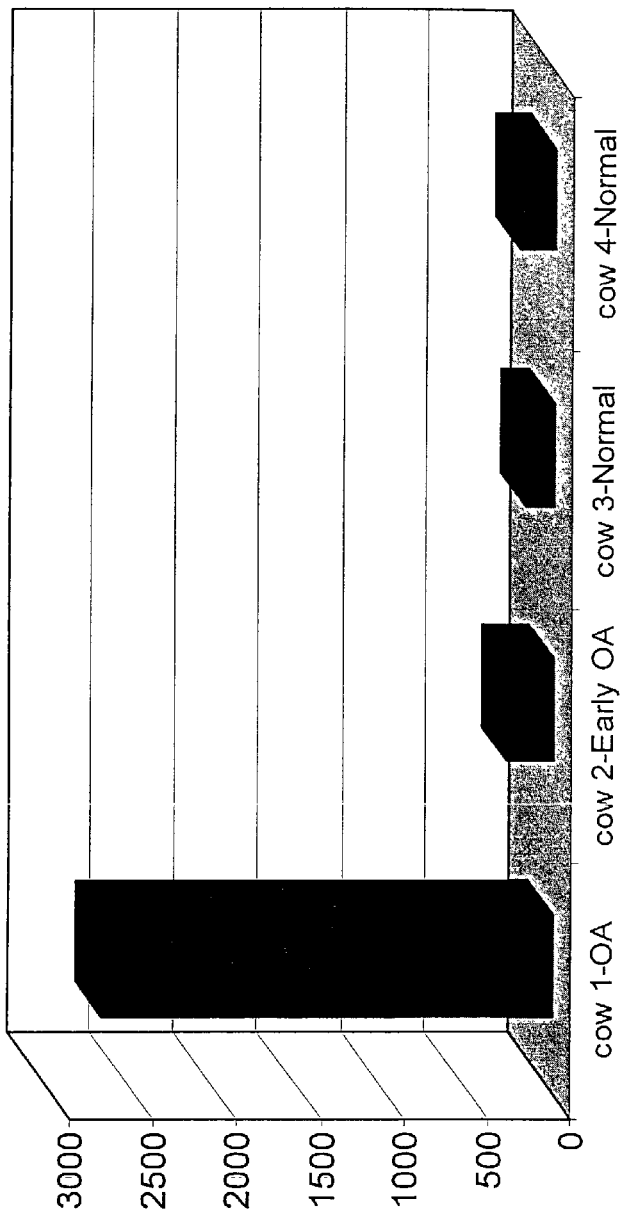
FIG. 8 is a bar graph illustrating the relative abundance of the collagen type II target peptide SEQ. ID. NO: 3 in cow urine.

FIG. 8 is a bar graph illustrating the relative abundance of a post-translational modification of peptide SEQ. ID. NO: 3 in the urine from four different cows as determined by analytical methods of the present invention. The relative abundance of the peptide was graphed in a manner similar to the graph shown in FIG. 4. The relative abundance of the target peptides, as determined by its measured areas under the curves was compared in the bar graph. Cow-1 exhibited signs and symptoms of arthritis; cow-2 exhibited early signs and symptoms of arthritis; cow-3 and cow-4 did not exhibit signs and symptoms of arthritis. The relative abundance of the target peptide was nearly five (5) times greater in the urine from cow-1 than cow-2. The relative abundance of the post-translationally-modified peptide SEQ ID NO: 3, having 4-hydroxyproline at positions 14 and 26, in cow-2 exhibiting early signs and symptoms of arthritis is greater than that of cow-3 and cow-4, normal cows having no detectable signs and symptoms of arthritis.

Figure 9:
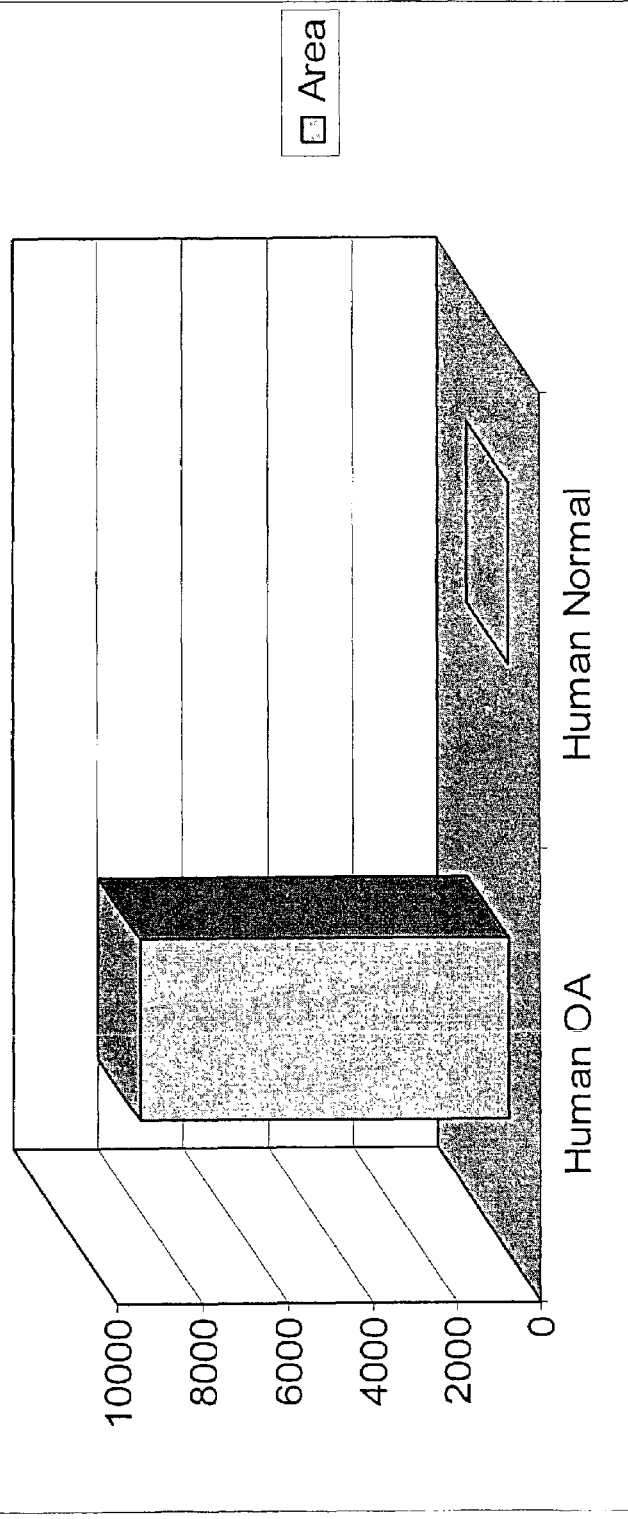
FIG. 9 is a bar graph illustrating the relative abundance of the collagen type II target peptide SEQ. ID. NO: 2 in human urine.

FIG. 9 is a bar graph illustrating the relative abundance of the post-translation analog of peptide SEQ ID NO: 2, having 4-hydroxyproline at positions 14 and 26, in human urine. As shown, the relative abundance of the peptide in urine from normal humans was not detected and is shown to be 0; the relative abundance of the peptide in the urine of the human subject diagnosed with and demonstrating signs and symptoms of osteoarthritis is 8000.

Figure 10:
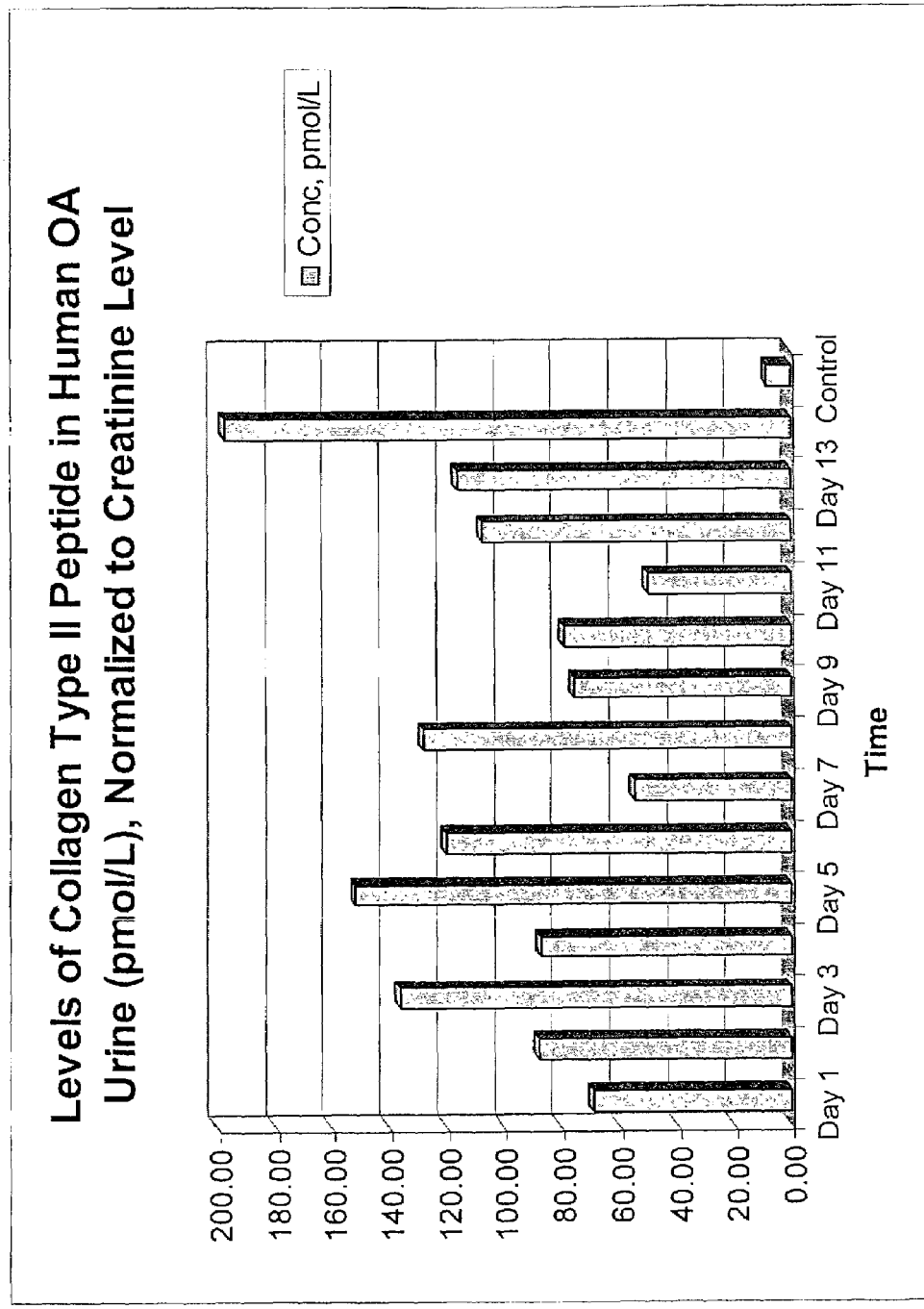
FIG. 10 is a bar graph illustrating the relative abundance of the collagen type II target peptide SEQ ID NO: 2 in human urine; First pass urine was collected daily over a period of 14 days to test the day-to-day variation of the peptide abundance, normalized for creatinine levels.

FIG. 10 is a bar graph illustrating temporal levels of collagen type II peptide (SEQ ID NO: 2) in the urine of a human medically diagnosed with and exhibiting signs and symptoms of osteoarthritis. The peptide level varies from 60–200 pmol/mL over a 14 day period, and is much higher in abundance than the level in a control human urine sample. The results plotted on the graph indicate the validity and usefulness of the peptide as a biomarker. Determination of the biomarker level over time can indicate a progression or regression of disease. Changes in the biomarker level can be used to evaluate the effectiveness of treatments. For example, with reference to FIG. 9, successful treatment of the subject with an MMP-13 inhibitor would result in a reduction in the relative level of collagen type II peptide in a biological sample taken from the patient. It will be appreciated that these uses of the novel biomarkers are illustrative of the usefulness of the biomarker. Any useful applications of the biomarkers and methods of identification and quantification described herein, are intended to be included within the scope of the invention.

It will be appreciated by those skilled in the art that characteristic and identifiable derivatives or modifications of the novel biomarkers of the present invention can be produced using recognized techniques. For example, any of the peptides represented by SEQ ID NO: 2 through SEQ ID NO: 43 or their post-translational analogs could be enzymatically or chemically cleaved to yield one or more derivatives that would be readily identifiable. Such a derivative consequently could function as a biomarker. Likewise, for example, any of the peptides represented by SEQ ID NO: 2 through SEQ ID NO: 43 or their post-translational analogs could be modified, for example by changing, substituting, adding, or deleting one or more amino acid residues, resulting in an identifiable modified peptide that could function as a biomarker.

It also will be understood by those skilled in the art that there are other potential modifications to the peptides of the present invention that could change their physical properties (e.g., hydrophobicity, molecular weight, etc.) and thereby impart advantages to purification or detection of the target peptides. These modifications could result from derivatization of biological fluids, including urine and blood, or extracts of biological fluids to modify specific amino acid residues on the target peptides. Directed sites of modification may include, without limitation: a hydroxyl group on hydroxyproline or serine; an amino group on lysine or at a target peptide N-terminus; a guanidyl group on arginine; a carboxamidyl group on glutamine; a carboxylic acid group on aspartic acid or glutamic acid or at a target peptide C-terminus; and any combination of such modifications.

Examples of modifications of amino acid side chains by chemical derivatization have been described in references and are known to persons skilled in the art (D. Knapp, *Handbook of Analytical Derivatization Reactions*, John Wiley and Sons, Inc. (1979), incorporated herein by reference). Reagents used for chemical derivatization of amino acid side chains are commercially available. An example of one known commercial provider of these reagents is Pierce Chemical Company, Rockford, Ill.

Amino acids that comprise the peptides of the present invention may be modified due to chemical instability in the biological fluid or extract. Examples of modifications include conversion of aspartic acid to isoaspartic acid and cyclization of glutamine. Quantification of peptides of the present invention that have been modified by these chemical conversions is included within the scope of the invention.

Peptides of the present invention may be hydrolyzed by chemical or enzymatic methods to produce shorter peptides that are then purified and/or detected. By way of example, proteases including amino-peptidases, carboxy-peptidases, arg-C proteinase such as, for example clostripain (Clostridiopeptidase B), asp-N endopeptidase, chymotrypsin, lys-C proteinase, papain' pepsin, proline-endopeptidase, proteinase K, staphylococcal peptidase I, thermolysin, thrombin, and trypsin may be used to hydrolyze the target peptides to shorter forms, which may then be detected and quantified as a marker of in vivo collagenase activity. (B. Keil, *Specificity of proteolysis*, Springer-Verlag Berlin-Heidelberg-New York, pp.335. (1992), incorporated herein by reference). By way of example, a lys-C proteinase may be used to hydrolyze the target peptides on the C-terminal side of lysine to generate two shorter peptides, which can then be quantified. Glutamyl endopeptidases (Glu-C or V8) also may be used to cleave the target peptide at the C-terminal side of glutamic acid or aspartic acid to generate two or more shorter peptides, which then can be quantified. (J. Birktoft and K. Breddan, Glutamyl endopeptidases, *Methods of Enzymology*, 244:114–126 (1994); J. Houmard and G. Drapeau, Stapylococcal protease: a proteolytic enzyme specifc for glutamoyl bonds, *Proceedings of the National Academy of Science of the United States of America*, 69:3506–3509 (1972), incorporated herein by reference). The present invention includes but is not limited to detection and quantification of hydrolysis products of the target peptides embodied in this document through use of the aforementioned proteases. Also for the purposes of further example, formic acid can be used to cleave target peptides adjacent to aspartic acid residues to generate shorter peptides for quantification. (Li, A. et al., Chemical cleavage at aspartyl residues for protein identification, *Anal. Chem*, 73: 5395–402 (2001), incorporated herein by reference).

The foregoing are provided as examples of modifications and derivatives of peptides of the present invention and do not include all potential modifications or derivatives of the peptides of the present invention that would be recognized by one skilled in the art. Consequently, the present invention includes detection and/or quantification of these, and any other modifications and derivatives of the peptides of the present invention, as well as those derived or modified peptides themselves when used for the purpose of quantifying the biomarkers of the present invention.

Figure 11:
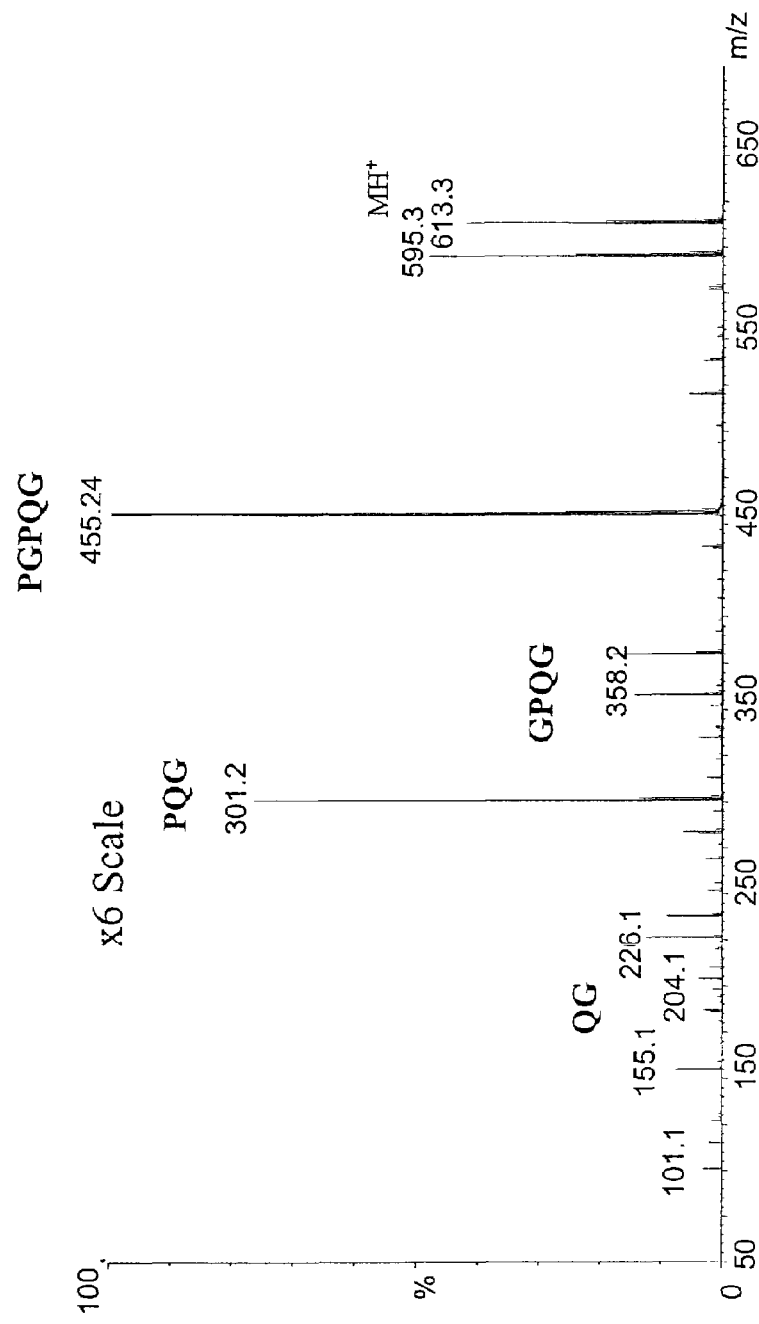
FIG. 11 illustrates the fragment ions of a synthetic collagen type I peptide SEQ ID NO: 12 produced by tandem mass spectrometry.
Figure 12:
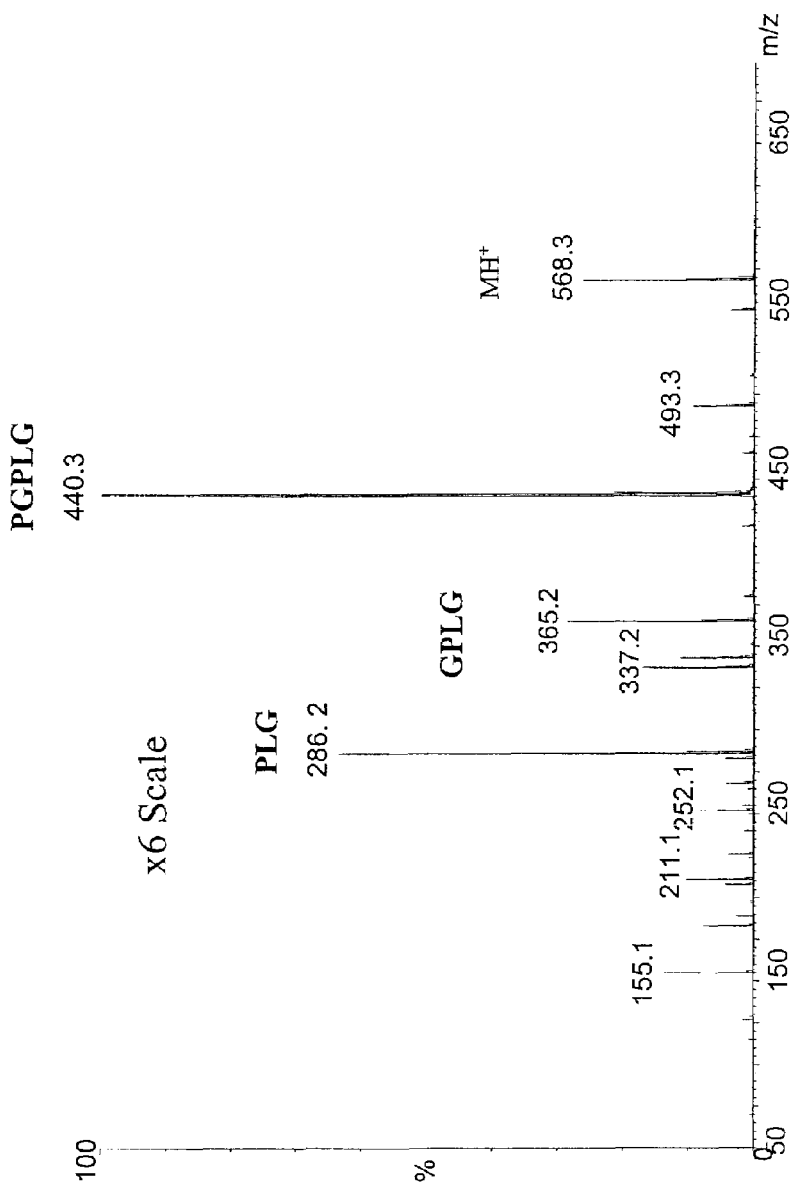
FIG. 12 illustrates the fragment ions of a synthetic collagen type III peptide SEQ ID NO: 13 produced by tandem mass spectrometry.

The analytic principles of the present invention also can be used to identify and quantify peptides which may serve as biomarkers of breakdown of collagens other than collagen type II. The peptide sequence Gly-Thr-Pro-Gly-Pro-Gln-Gly (SEQ ID NO: 12) is the expected C-terminus sequence of a biomarker peptide resulting from metalloproteinase cleavage of collagen type I, based upon an analysis of the peptide database. FIG. 11 illustrates the characteristic fragment ions resulting from the collisional activation of synthesized SEQ ID NO: 12. Collagen type I breakdown peptides can be identified in a biological sample using the methods of the present invention based upon the identification of characteristic fragment ions of m/z 301 and 455 for the non-hydroxylated form and m/z 301 and 471 for the hydroxylated form. Likewise, FIG. 12 illustrates that the peptide C-terminal sequence Gly-Ala-Pro-Gly-Pro-Leu-Gly (SEQ ID NO: 13) expected from the enzymatic cleavage of collagen type III will also yield identifiable, characteristic fragment ions when analyzed by methods of the present invention. The collagen type III fingerprint fragment ions are m/z 286 and 440 for the non-hydroxylated form and would be m/z 286 and 471 for the hydroxylated form. FIGS. 12 and 13 not only identify characteristic fragment ions that can be used to identify breakdown peptides specifically from collagen types I and III, respectively, but also substantiate the fact that the methods of the present invention can be employed more broadly to identify characteristic cleavage products of any collagen.

EXAMPLE 5

Alternative Embodiment Of Method of Identifying and Quantifying Collagen Type II Biomarker Peptides Sample Preparation 1. For standard calibration curve generation, two mL of normal female (30 years old) human urine was spiked with 50 ng internal standard (deuterated 30 amino acid peptide SEQ ID NO: 2 and 45 amino acid peptide SEQ ID NO: 16, containing from 5ng to 100 ng of collagen type II 30 amino acid peptide SEQ ID NO: 2 (2 hydroxyprolines) and 45 amino acid peptide SEQ ID NO: 16 (5 hydroxyprolines) peptides (N=2).
2. Unknown urine samples (two mL) were spiked with 50 ng internal standard. Each urine standard and unknown was placed into a Centriconâ membrane centrifugal filter device (YM-3, 2mL capacity with 3000 MW cut off, Millipore Co., Bedford, Mass.) and was centrifuged at 5,000 rpm (5,000 g) using a Speedfugeâ (HSC, 10KA, Savant Instruments, Farmingdale, N.Y.) with water cooling. Prior to the urine filtration, each Centriconâ was pre-wetted with 50 uL of 1% formic acid solution.
3. After 9 0% o f t he urine was filtered by centrifugation, about 2 00 uL o f t he retained solute solution (concentrated solute) remained in the retentate vial. One mL of water containing 1% (v/v) formic acid was added to the retentate and it was further centrifuged until approximately 200 uL of the solute solution remained.
4. The solute solution (retentate) was then transferred to a reaction-vial and evaporated to dryness under nitrogen.

Each dried sample was dissolved in 100 uL of water containing 1% (v/v) formic acid and transferred t o an HP autosampler vial with an insert. The filtrate was discarded.

HPLC/MS/MS

1. A sample aliquot (20 uL) from the autosampler vial was injected onto a Betasil C-18 column (ThermoHypersil-Keystone Co., Bellefonte, Pa., 5 micron particle size, 200×2 mm) that was connected to a Rheas 2000 HPLC system (Leap Technologies, Carrbore, N.C.) interfaced with an ABI Sciex 4000 MS/MS spectrometer.
2. Elution was accomplished by ramping the mobile phases (A=water/1% formic acid; B=acetonitrile/1% formic acid) from 5% B to 35% B in 5 minutes and holding for 2 minutes.
3. The column was re-equilibrated by ramping the gradient back to 5% B in 0.5 minutes and holding for 4.5 minutes before injection of the next sample. 4. Three MRM ion pairs (1039/301, 1039/471, and 1039/568; 1040/306, 1040/476, 1040/573; 914/301, 914/471, and 914/568; 916/306, 916/476, 916/573) were monitored for each of the four peptides (45 mer (5OH) (SEQ ID NO: 16, d5–45 mer (5OH) (SEQ ID NO: 16) internal standard, 30 mer (2OH) (SEQ ID NO: 2), and d5–30 mer (2OH) (SEQ ID NO: 2) internal standard), respectively, with a 200 ms dwell time for each ion pair at low resolution modes for parent and product ions.
5. The integrated peak areas of the three ion pairs for each peptide were determined by Sciex Analyst 1.2 software, and the summed, integrated peak areas of the two analyte peptides were normalized by the summed, integrated peak areas of the deuterated internal standard peptides and compared to the standard calibration curve to determine the quantities of 30 mer (SEQ ID NO: 2) and 45 mer (SEQ ID NO: 16) collagen II peptides in each unknown sample. The HPLCS/MS analysis assay for each sample was performed in duplicate.

It will be appreciated that the method described in Example 5 was illustrated using human urine samples and the results set out in Example 6. The method can be used to identify and quantify peptide biomarkers in the urine of other species, as shown by Examples 7 through 12, below. One skilled in the art will note that appropriate, species-specific standard peptides will be employed when testing for the presence of peptide biomarkers in other species.

EXAMPLE 6

Identification and Quantification Of Collagen II Peptides In Human Urine

Identification and quantification of additional collagen type II peptide fragments in urine samples of humans was performed according to the method described in Example 5. The following peptides were found in detectable amounts in human subjects medically diagnosed with and displaying signs and symptoms of arthritis:

Lys-Gly-Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 15), where in the most abundant form positions 10, 16, 25, 31 and 42 are 4-hydroxyproline;

Ala-Arg-Gly-Asp-Ser-Gly-Pro-Pro-Gly-Arg-Ala-Gly-Glu-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-

Gly-Pro-Pro-Gly-Pro-Gln-Gly (SEQ ID NO: 16), where in the most abundant form positions 8, 14, 23, 29 and 41 are 4-hydroxyproline; and Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 17), where in the most abundant form positions 12 and 24 are 4-hydroxyproline.

Peptide SEQ ID NO.: 16 has been found to be the most abundant collagen II neoepitope peptide measured in human urine.

EXAMPLE 7

Identification and Quantitification Of Collagen II Peptides In Bovine Urine

Identification and quantification of additional collagen type II peptide fragments in urine samples of cattle was performed according to the method described in Example 5. The following peptides were found in detectable amounts in bovine subjects medically diagnosed displaying signs and symptoms of arthritis:

Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 34), where in the most abundant form positions 10, 16, 25, 28, and 43 are 4-hydroxyproline and position 43 is hydroxylysine; and Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 35), where in the most abundant form positions 8,14,23,29 and 41 are 4-hydroxyproline and position 26 is hydroxylysine. Peptide SE ID NO: 35 is the most abundant collagen II neoepitope peptide measured in bovine urine.

EXAMPLE 8

Identification and Quantitification Of Collagen II Peptides In Canine Urine

Identification and quantification of collagen type II peptide fragments in urine samples of dogs was performed according to the method described in Example 5. The following peptides were found in detectable amounts in canine subjects displaying signs and symptoms of arthritis:

Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 18), where in the most abundant form positions 10, 16, 25, 31 and 43 are 4-hydroxyproline and position 28 is hydroxylysine;

Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 19), where in the most abundant form positions 8, 14, 23, 29, and 41 are 4-hydroxyproline and position 26 is hydroxylysine;

Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 20), where in the most abundant form positions 4, 10 and 22 are 4-hydroxyproline and position 10 is hydroxylysine;

Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 21), where in the most abundant form positions 2, 8 and 20 are 2-, 3- or 4-hydroxyproline and position and position 5 is 4-hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 22), where in the most abundant form position 2 is hydroxylysine and positions 5 and 17 are 4-hydroxyproline. Peptide SEQ ID NO: 19 is the most abundant collagen II neoepitope peptide measured in canine urine.

EXAMPLE 9

Identification and Quantification Of Collagen II Peptides In Feline Urine

Identification and quantification of collagen type II peptide fragments in urine samples of cats was performed according to the method described in Example 5. The following peptides were found in detectable amounts in feline subjects displaying signs and symptoms of arthritis:

Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 23), where in the most abundant form positions 10, 16, 25, 31 and 43 are 4-hydroxyproline and position 28 is hydroxylysine;

Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 24), where in the most abundant form positions 8, 14, 23, 29 and 41 are 4-hydroxyproline and position 26 is hydroxylysine;

Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 25), where in the most abundant form positions 8, 14 and 26 are 4-hydroxyproline and position 11 is -hydroxylysine;

Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 26), where in the most abundant form positions 4, 10 and 22 are 4-hydroxyproline and position 7 is hydroxylysine; and Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 27), where in the most abundant form positions 2, 8, and 20 are 4-hydroxyproline and position 5 is hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 28), where in the most abundant form position 2 is hydroxylysine and positions 5 and 17 are 4-hydroxyproline.

Peptide SEQ ID NO: 24 is the most abundant peptide neoepitope found in urine of feline subjects.

EXAMPLE 10

Identification and Quantification Of Collagen II Peptides In Equine Urine

The presence of collagen type II peptide SEQ ID NO: 11 was confirmed and identification and quantification of additional collagen type II peptide fragments in urine samples of horses was performed according to the method described in Example 5. The following peptides also were found in detectable amounts in equine subjects displaying signs and symptoms of arthritis:

Lys-Gly-Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-

Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 29), where in the most abundant form positions 10, 16, 25, 31 and 43 are 4-hydroxyproline and position 28 is -hydroxylysine;

Ala-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 30), where in the most abundant form positions 8, 14, 23, 29 and 41 are 4-hydroxyproline and position 26 is hydroxylysine;

Ala-Gly-Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 31), where in the most abundant form positions 4, 10 and 22 are 4-hydroxyproline and position 7 is hydroxylysine;

Pro-Pro-Gly-Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 32), where in the most abundant form positions 2, 8, and 20 are 4-hydroxyproline and positions 26 is hydroxylysine; and Glu-Lys-Gly-Glu-Pro-Gly-Asp-Asp-Gly-Pro-Ser-Gly-Pro-Asp-Gly-Pro-Pro-Gly-Pro-Gln-Gly (SEQ ID NO: 33), where in the most abundant form position 2 is hydroxylysine and positions 5 and 17 are 4-hydroxyproline.

Peptide SEQ ID NO: 30 is the most abundant collagen II neoepitope peptide found in equine urine.

EXAMPLE 11

Identification and Quantification Of Collagen II Peptides In Rat Urine

The following peptides also were found in detectable amounts in rats displaying signs and symptoms of arthritis:

Ala-Pro-Gly-Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 39), where in the most abundant form positions 2, 8 and 20 are 4-hydroxyproline and position 5 is hydroxylysine;

Glu-Lys-Gly-Glu-Pro-Gly-Asp-Asp-Gly-Pro-Ser-Gly-Ser-Asp-Gly-Pro-Pro-Gly-Pro-Gln-Gly (SEQ ID NO: 40), where in the most abundant form position 2 is hydroxylysine and positions 5 and 17 are 4-hydroxyproline;

Gly-Glu-Pro-Gly-Asp-Asp-Gly-Pro-Ser-Gly-Ser-Asp-Gly-Pro-Pro-Gly-Pro-Gln-Gly (SEQ ID NO: 41), wherein positions 3 and 15 are 4-hydroxyprolines; and Asp-Gly-Pro-Ser-Gly-Ser-Asp-Gly-Pro-Pro-Gly-Pro-Gln-Gly (SEQ ID NO: 42), where in the most abundant form position 10 is 4-hydroxyproline.

Peptide SEQ ID NO: 42 is the most abundant collagen II neoepitope peptide measured in rat urine.

EXAMPLE 12

Identification and Quantification Of Collagen II Peptides In Guinea Pig Urine

Identification and quantification of collagen type II peptide fragments in urine samples of guinea pigs was performed according to the general method described in Example 5. The following peptide was found in detectable amounts in guinea pigs displaying signs and symptoms of arthritis:

Val-Arg-Gly-Asp-Ser-Gly-Pro-Pro-Gly-Arg-Ala-Gly-Asp-Pro-Gly-Leu-Gln-Gly-Pro-Ala-Gly-Pro-Pro-Gly-Glu-Lys-Gly-Glu-Pro-Gly-Asp-Asp-Gly-Val-Ser-Gly-Ala-Asp-Gly-Pro-Pro-Gly-Pro-Gln-Gly (SEQ ID NO: 43), where in the most abundant form positions 8, 14, 23, 20 and 41 are 4-hydroxyprolines and position 26 is hydroxylysine.

From the foregoing disclosure, it will be seen that we have isolated and determined the amino acid sequences of specific proteolytic cleavage peptides represented by SEQ ID NO: 2, SEQ ID NO: 3, SEQ ID NO: 4, SEQ ID NO: 8, SEQ ID NO: 9, SEQ ID NO: 10, SEQ ID NO: 11 , SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43 and post-translational modifications thereof.

It will be appreciated by those skilled in the art that because the complete amino acid sequences of specific peptides formed by proteolytic cleavage of type II collagen of several animals have been determined in accordance with the present invention, and because a method of general applicability has been disclosed for determining other specific peptides formed by proteolytic cleavage of other collagens, numerous methods may now be used to identify and quantify these specific peptides in biological samples or biological extracts.

The tandem mass spectrometric method used in the discovery of the specific peptides disclosed herein may of course be used to identify and quantify them and other specific proteolytic cleavage peptides. This method has the advantages over present immunological methods that it can identify and quantify the specific peptides formed by proteolytic cleavage, not just the family of peptides sharing a common C-terminus found by existing methods; that it reliably identifies and quantifies post-translational modifications of the peptides; and that it does not require preparation of separate antibodies for different mammalian species. The spectrometric methods may, of course, identify and quantify the peptides by the use of derivatives and modifications as discussed above, either by treating the sample or extract to produce a derivative or modification of the peptide or peptides, or else by using them as standards.

Those skilled in the art will recognize other methods, within the scope of the invention, of identifying and quantifying the peptides. For example, known ultraviolet spectroscopy, electrochemical, or fluorescent methods may be employed with or without chromatography within the scope of the invention. Known sequencing methods are also included within the scope of the invention. Also, immunospecific antigen (ELISA) or other radioimmunoassay techniques that recognize specific peptide sequences or post-translational modifications thereof may be employed. For example, a neoepitope antibody to the N-terminus of the peptide, with or without a capture antibody, may provide greater sensitivity and specificity than current ELISA methods that use a C-terminal neoepitope antibody and a capture antibody to a portion of the sequence. By way of example, a neoepitope antibody directed against the N-terminus of one of the peptides may be prepared and utilized for identifying and quantifying the peptide. If the antibody is directed against the seven amino acid N-terminal sequence of the human peptide having SEQ ID NO: 16, or against the eight amino acid N-terminal sequence of the human peptide having SEQ ID NO: 2, it will provide unique identification of the peptide having that sequence. Because those terminal portions of the corresponding cat peptides (SEQ ID NO: 23 and SEQ ID NO: 25), dog peptides (SEQ ID NO: 18 and SEQ ID NO: 4), horse peptides (SEQ ID NO: 29 and SEQ ID NO: 11), and cow peptides (SEQ ID NO: 34 and SEQ ID NO: 3) are conserved, these peptides can also be specifically identified so long as the source of the biological sample or biological extract is known. If the antibody is directed against a shorter N-terminal sequence, positive identification of the peptide will require the use of some other technique, such as the use of a second antibody directed against the C-terminus or against an intermediate "capture region" as in a sandwich ELISA method. The methods for producing the needed antibodies are well known in the art. For example, the methods used by Otterness et al, supra, to form antibodies directed to the C-terminus of the degradation peptides may be utilized to form antibodies to the N-terminus.

By using the tandem mass spectrometric methods disclosed herein, the specific peptides produced by proteolytic cleavage of other collagens (including collagens from other animals, as w ell as type I and type III collagens) can easily be ascertained, and these specific peptides can then be identified by any of the foregoing methods.

Although the illustrative examples involved the identification and quantification of the peptides in urine samples, the peptides may be detected in other biological fluid samples or extracts, such as blood, plasma, or synovial fluid. Also, samples of tissues, such as tissue around a joint, may be obtained by biopsy or the like, and the peptides isolated through techniques known to the art. Identification and quantification of the biomarkers carried out by methods of the present invention then may be employed to identify and quantify the biomarkers in the tissue sample. Consequently, as used herein, the term biological sample is intended to include any sample of a body fluid or body tissue in which the biomarkers can be identified and quantified.

This quantification of the peptides can be used for diagnosis or prognosis of diseases such as osteoarthritis or rheumatoid arthritis, to monitor collagenase enzyme activity in disease or physiological conditions characterized by collagenase activity, and to evaluate drugs or agents used to inhibit collagen degradation, such as matrix metalloproteinase inhibitors, or the levels of active collagenase, particularly those drugs or agents that result in the inhibition of collagen degradation. Consequently, the peptides SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43 and their post-translational modifications in biological samples are biomarkers of disease or conditions in which collagen type II proteolysis is characteristic. The identification and quantification of the biomarker peptides can be used in diagnosis and prognosis of diseases or conditions characterized by collagen II degradation.

Further, the identification and quantification of the biomarkers peptides SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43 and their post-translational modifications, for example, in a biological sample can be used to monitor or evaluate the efficacy of a drug or other agent used to block the activity and/or abundances of the proteolytic enzyme(s) that yields the degradation products, peptides SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43 and their post-translational modifications.

One exemplary use of the biomarker of the present invention is to monitor and evaluate the activity of a matrix metalloproteinase inhibitor (MMPi). The identification and quantification of peptides represented by SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43 or post-translational modifications, in biological fluid samples can indicate collagen type II degradation and the relative in vivo activity of a collagenase enzyme, for example MMP-13. In diseases or physiologic conditions in which collagen type II degradation is a pathological characteristic, administration of a pharmacologically effective amount of an MMP inhibitor, for example, an MMP-13 inhibitor, should result in the reduction or elimination of peptide Leu-Gln-Gly-Pro-Ala-Gly-Pro-Pro-Gly-Glu-Lys-Gly-Glu-Pro-Gly-Asp-Asp-Gly-Pro-Ser-Gly-Ala-Glu-Gly-Pro-Pro-Gly-Pro-Gln-Gly (SEQ ID NO: 2), for example, in a human subject's biological fluid sample.

The invention claimed is:

1. A method of detecting enzymatic proteolysis of a collagen, the method comprising identifying and quantifying a specific peptide proteolysis product of the collagen occurring in a biological sample or biological extract, wherein the specific peptide proteolysis product is selected from the group consisting of SEQ ID NO: 2, 15, 16 and 17.

2. A method of detecting enzymatic proteolysis of a collagen, the method comprising identifying and quantifying a specific peptide proteolysis product of the collagen occurring in a biological sample or biological extract, wherein the biological specimen or biological extract is from a human subject, the method comprising the identification and quantification of the peptide SEQ ID NO: 2.

3. A method of detecting enzymatic proteolysis of a collagen, the method comprising identifying and quantifying a specific peptide proteolysis product of the collagen occurring in a biological sample or biological extract, wherein the biological specimen or biological extract is from a human subject, the method comprising the identification and quantification of the peptide SEQ ID NO: 15.

4. A method of detecting enzymatic proteolysis of a collagen, the method comprising identifying and quantifying a specific peptide proteolysis product of the collagen occurring in a biological sample or biological extract, wherein the biological specimen or biological extract is from a human subject, the method comprising the identification and quantification of the peptide SEQ ID NO: 16.

5. A method of detecting enzymatic proteolysis of a collagen, the method comprising identifying and quantifying a specific peptide proteolysis product of the collagen occurring in a biological sample or biological extract, wherein the biological specimen or biological extract is from a human subject, the method comprising the identification and quantification of the peptide SEQ ID NO: 17.

6. The method of claim 1 further comprising forming a derivative or modification of the specific peptide proteolysis product in the sample or extract before identifying and quantifying the peptide.

7. The method of claim 1 wherein the collagen is human type II collagen and the specific peptide has a C-terminus represented by SEQ ID NO: 17.

8. The method of claim 4 wherein the peptide comprises a post-translational modification comprising hydroxylation of at least one proline.

9. The method of claim 4 wherein the peptide comprises a post-translational modification comprising hydroxylation of lysine.

10. A method of detecting enzymatic proteolysis of a collagen, the method comprising specifically detecting the peptide SEQ ID NO: 16 in a biological sample or biological extract.

11. The method of claim 10 wherein the peptide comprises a post-translational modification comprising hydroxylation of at least one proline.

12. The method of claim 10 wherein the peptide comprises a post-translational modification comprising hydroxylation of lysine.

13. The method of claim 6 wherein the specific peptide is SEQ ID NO: 2, SEQ ID NO: 15, SEQ ID NO: 16, or SEQ ID NO: 17.

14. A method of detecting enzymatic proteolysis of a collagen, the method comprising specifically detecting the peptide SEQ ID NO: 16 in a biological sample or biological extract.

15. A method of detecting enzymatic proteolysis of a collagen, the method comprising specifically detecting the peptide SEQ ID NO: 2 in a biological sample or biological extract.

16. A method of detecting enzymatic proteolysis of a collagen, the method comprising specifically detecting the peptide SEQ ID NO: 15 in a biological sample or biological extract.

17. A method of detecting enzymatic proteolysis of a collagen, the method comprising specifically detecting the peptide SEQ ID NO: 17 in a biological sample or biological extract.

* * * * *